US006536272B1

(12) United States Patent
Houston et al.

(10) Patent No.: US 6,536,272 B1
(45) Date of Patent: Mar. 25, 2003

(54) WATER MONITORING, DATA COLLECTION, AND TRANSMISSION MODULE

(75) Inventors: Thomas Houston, Miami, FL (US); Rod G. Zika, Miami, FL (US); Geoffrey K. Morrison, Miami, FL (US); Richard Wood, N Miami Beach, FL (US); Arthur M. Barbeito, Miami, FL (US)

(73) Assignees: University of Miami, Miami, FL (US); International Society of Ocean Monitoring and Research, Miami, FL (US)

( * ) Notice: Subject to any disclaimer, the term of this patent is extended or adjusted under 35 U.S.C. 154(b) by 76 days.

(21) Appl. No.: 09/633,065

(22) Filed: Aug. 4, 2000

Related U.S. Application Data

(60) Provisional application No. 60/147,334, filed on Aug. 6, 1999.

(51) Int. Cl.⁷ .................................................. G01F 1/00
(52) U.S. Cl. ...................................... 73/170.29; 702/2
(58) Field of Search ................. 702/2, 5, 3; 73/170.29, 73/170.33, 170.34

(56) References Cited

U.S. PATENT DOCUMENTS

| | | | |
|---|---|---|---|
| 5,283,767 A | * | 2/1994 | McCoy .................... 73/170.34 |
| 5,578,751 A | * | 11/1996 | French .................... 73/170.29 |
| 5,808,916 A | * | 9/1998 | Orr et al. .................... 703/6 |

* cited by examiner

Primary Examiner—Donald E. McElheny, Jr.
(74) Attorney, Agent, or Firm—Nixon & Vanderhye PC

(57) ABSTRACT

A water sampling apparatus is disclosed having a water inlet and a water collecting scoop. A pump, in fluid communication with the water inlet, draws a water sample from a body of water through the water inlet. A plurality of testing units, in fluid communication with the pump and the water inlet, determine characteristics of a the water sample. The plurality of testing units are contained within an instrument module. A plurality of electrical components, in communication at least with some of the plurality of testing units, generates data signals concerning the characteristics of the water sample. The plurality of electrical components are contained within a computer module. A computer, in communication at least with some of the plurality of electrical components, collects the data signals generated by the plurality of electrical components and provides the data signals both to a local database and also by satellite transmission to a remote central data base. An automated anti-bio fouling system and an automatic sensor calibration system are also discussed. A water outlet, in fluid communication with the plurality of testing units, returns the water sample to the body of water.

22 Claims, 17 Drawing Sheets

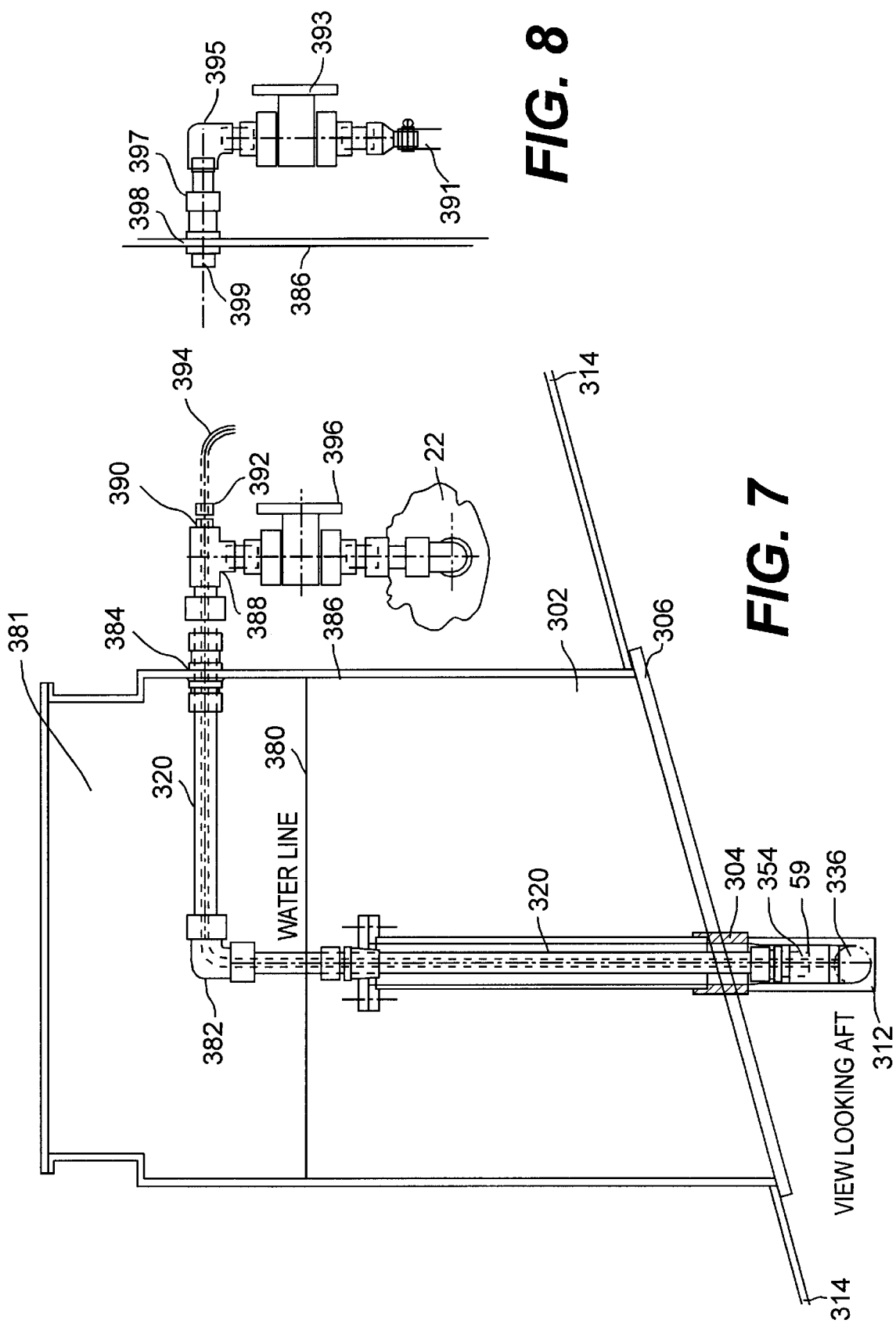

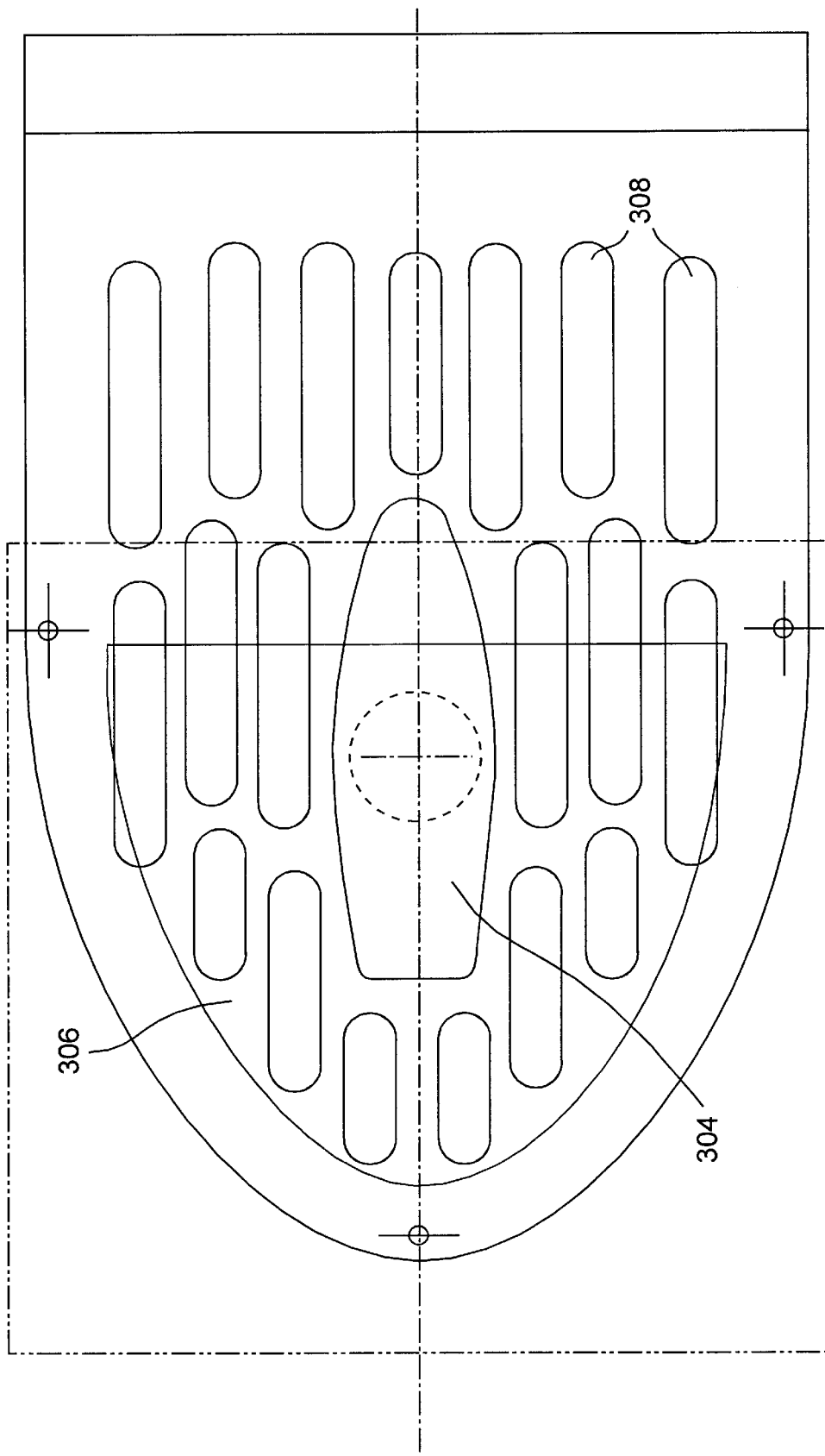

WATER MONITORING, DATA COLLECTION, AND TRANSMISSION MODULE

CROSS-REFERENCE

This application relies on U.S. Provisional Application No. 60/147,334, filed Aug. 6, 1999, (including its specification and drawings) for priority. That application is hereby incorporated into this application by reference.

FIELD OF THE INVENTION

The invention relates to an apparatus and method for sampling seawater and freshwater characteristics. More specifically, the present invention concerns the automated acquisition and transmission of data from a sea-going vessel.

BACKGROUND OF THE INVENTION

Traditional observation and measurement of physical, chemical and biological properties of bodies of water including coastal and open ocean environments, lakes, rivers, and reservoirs has been carried out historically by at least two techniques.

First, a single sensor (or a limited number of sensors) may be embedded in a device immersed in the water (in drifters, buoys, or devices dragged behind vessels) to periodically sample the water. However, drifters are expendable with a limited lifetime and costly, and because they move with the currents, are capable of collecting data only from limited areas of oceans and other bodies of water. Buoys are stationary and can only collect data from a fixed location. Dragged devices are very difficult to use and are often lost.

Second, research vessels (which are very large and expensive to operate) may be equipped with various sensing devices and computers for collecting and storing water condition data. However, vessels of this sort are very expensive. Not only are they costly to build, but, because of the large, technically-trained crews they require, they are also very expensive to operate. In addition, because of the manner in which the data is collected, vessels of this type often require a considerable amount of time to assemble and disseminate the information.

Accordingly, due to a lack of observational resources and effort, broad, synoptic coverage of much of the world's oceans (particularly coastal areas), as well as other bodies of water, has remained elusive.

Historically surface water sampling for ships underway has been accomplished by drawing the water into the vessel through a sea chest, through a temporary hose over the side rail, through an open hole in the vessel's hull, in some cases with a pipe projecting through the hole into the free water away from the ship's hull, or by means of a pail thrown over the vessel's railing. All of these approaches give rise to any number of difficulties which make routine underway sampling of unadulterated surface water problematic. Such difficulties include contamination from the ship's hull or plumbing, limitation on the vessel's speed for which sampling can be performed, excessive bubbling or cavitation problems, excessive bio-fouling which modifies the sampled water, and inaccurate temperature measurements due to temperature modification along the water's flow path from the sampling point to the measurement point.

Accordingly, a need has developed for an apparatus that overcomes many of these difficulties. Specifically, a need has developed for a sampling apparatus that is largely automated, requires little or no technical training to operate and maintain, can accurately sample water with little or no contamination or degradation of that water during the sampling operation, and is relatively inexpensive.

SUMMARY OF THE INVENTION

It is, therefore, an object of the present invention to provide an automated testing apparatus that can autonomously sample water with little or no contamination of that water during the sampling operation.

It is a further object of the present invention to provide a solution to the problem of rapid deterioration of traditional monitoring and testing devices (and the related deterioration in the accuracy of their data) utilized (submersed or floating) in oceans and other bodies of water.

It is another object of the present invention to provide an apparatus that avoids the immense expense associated with current methods of monitoring the oceans and other bodies of water (e.g., $ 10,000+ a day for a research vessel and $ 30,000–50,000 for a drifter or buoy collecting only one or two types of data).

Another object of the present invention is to provide a solution to the need for large technically trained staff to man the water monitoring devices, such as on a research vessel.

Also, it is an object of the present invention to provide an apparatus that permits broad monitoring coverage of ocean or other bodies of water worldwide.

Moreover, it is an object of the present invention to provide an apparatus that can be effectively used by private individuals who wish to assist in ocean monitoring efforts to effectively utilize their own vessels as a research tool.

It is still another object of the present invention to provide an apparatus that may be widely deployed and may be capable of carrying many and various sensors that are easily and interchangeably used (snapped into) the sampling module.

Also, it is the objective of the present invention to provide a standard system that is compatible or can readily be made to be so, to operate with new or existing sensors from various companies, agencies, or individual research personnel.

Another object of the present invention is to provide an apparatus (or module) that encompasses a wide scope and breadth of data collection and transmission capabilities (multiple types of data).

One further object of the present invention is to provide a water monitoring module that is small and compact in size and, accordingly, is low in cost (e.g., $ 10,000–25,000), making it attractive to owners of private boats.

Another object of the present invention is the provision of a water sampling module that is durable and operates over a long lifetime.

Further objects of the present invention include the module's ability to operate autonomously without technically trained personnel, its ability to function in various areas and types of water including coastal areas of oceans, open ocean areas, aquaculture facilities and fresh water reservoirs, its ability to be directed by two-way communications, and its ability to accommodate many and various sensors, all operating off the module's standard power, light, anti-biofouling, calibration and software systems.

To accomplish these objectives, the present invention provides a water sampling apparatus that includes a water inlet and water collection device (scoop). A pump, in fluid communication with the water inlet, draws a water sample from a body of water through the water inlet. A plurality of testing units (sensors), in fluid communication with the pump and the water inlet, determine characteristics of a the water sample and are contained within an instrument module. A plurality of electrical components, in communication at least with some of the plurality of testing units, generate data signals concerning the characteristics of the water sample and are contained within a computer module. A computer, in communication at least with some of the plurality of electrical components, collects the data signals generated by the plurality of electrical components and provides the data signals to a database. A satellite communications system (or other communication system) in communications with the computer transmits all data gathered back to a centralized data receiving station. Finally, a water outlet, in fluid communication with the plurality of testing units, returns the water sample to the body of water.

A containment vessel and related automatic shut off valve are also provided by the present invention.

DESCRIPTION OF THE DRAWINGS

Various aspects and embodiments of the present invention are shown throughout the drawings, in which:

FIG. 7 is cross-sectional view of the present invention as illustrated in FIG. 6, taken along a vertical plane normal to the view in FIG. 6;

FIG. 8 is a side-view of the water return piping for the embodiment of the present invention illustrated in FIGS. 6 and 7;

FIG. 10 is a bottom plan view of the grate at the bottom of the trunk sea chest illustrated in FIGS. 6 and 7;

DETAILED DESCRIPTION OF THE PREFERRED EMBODIMENTS

Figure 1:
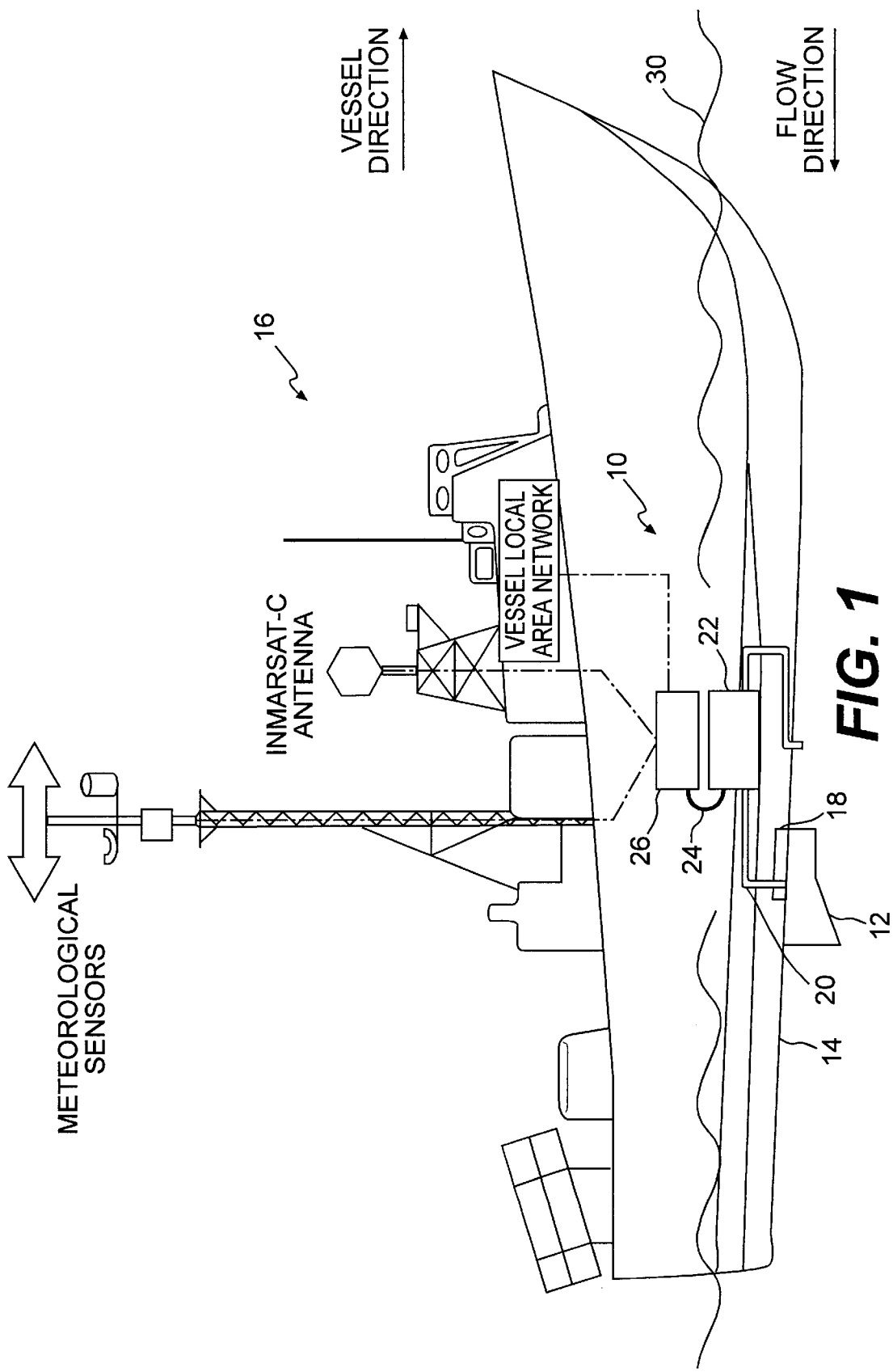
FIG. 1 is a side-view, schematic illustration of a sea-going vessel, showing one possible positioning of the sampling apparatus of the present invention thereon, the sampling apparatus being shown in exaggerated detail with respect to the size of the sea-going vessel.

Before delving into specific details, the apparatus of the present invention (which is also referred to as a "module" herein) is compact, integrated, autonomous, reliable, and durable. As such, it provides a much more comprehensive (in terms of areas covered and the magnitude and types of data collected) and significantly less expensive vehicle for monitoring oceans and other bodies of water than those currently in use.

In addition, because of its compact size, ease of installation, and autonomous method of operation, the apparatus presents an attractive option to potentially thousands of private boat owners, small businesses, and research agencies, all of whom are engaged in or would like to be engaged in oceanographic research.

At a minimum, the module accommodates many different sensors, operates with power from standard light and power sources, and incorporates automated calibration, anti-fouling, and control software systems, all of which are described in greater detail below.

The sampling apparatus is designed to collect, measure, and transmit data on various water characteristics including, but not limited to: temperature, salinity, oxygen, pH, redox, Eh, optical (beam attenuation and ocean color) and bio-optical parameters (e.g., Chlorophyll a), toxic heavy metals, $CO_2$ content, and other biological and biochemical characteristics. To do this, the module captures, prepares for analysis, and passes a stream of water through a collection of sensors that test for the various water characteristics.

Separately from collecting data concerning the water in which the sea-going vessel is positioned at any given time, the module also records local meteorological information and other pertinent data such as location of the vessel (through a Global Positioning System or "GPS"). Unlike other methods for testing and measuring the characteristics of seawater (which generally take the form of a series of individual and separate water monitoring devices deployed on large research ships, or a few isolated instruments placed aboard ocean buoys or other devices such as in-water drifters) the module is extremely compact, provides an internal system to fully integrate, regulate, and calibrate a large number of individual sensors, operates autonomously for extended periods of time, and is positioned out of the water so as to dramatically extend its operational lifetime. In addition, the module includes standardized software, power source(s), light source(s), calibration equipment, data sampling equipment, and anti-fouling systems for all of the sensors in the module.

Among others, the present invention is designed for use aboard private yachts and boats, cruise ships, commercial tankers, trawlers, fishing boats, piers, buoys, and other floating and fixed platforms. It is also contemplated that the present invention may be used to monitor aquaculture facilities, fresh water reservoirs, harbors, industrial and storm drain discharges into the ocean, and any other hydrologic situations where it is desirable to remotely monitor water conditions or characteristics.

Among the many features incorporated into the apparatus of the present invention, the module integrates the operation of several systems. First, the apparatus includes a water collection system comprising both a de-bubbler and external sensor housing ("scoop") that collects clean water—away from the hull surface of a vessel—strips off water debris, reduces the tendency for cavitation when a vessel moves at high speed, reduces bubble formation in the water stream, and accommodates a slide-in temperature probe. Second, the module accommodates a special antifouling system which uses Teflon® (polytetrafluoroethylene or PTFE) lined piping and electrical current charges to create chemical anti-fouling agents to prevent bio-fouling by marine and other organisms. Third, the module incorporates a calibration system that uses the chemical agents created by the anti-fouling system to provide calibration signals for some of the sensors. Fourth, the apparatus includes software programs that capture, format and transmit data in real time and regulate, operate, and maintain the various systems of the module. Fifth, the module includes a containment vessel mounted on the gate valve that penetrates the hull so that, in the event of a leakage in the piping, the containment vessel prevents water from freely entering the vessel.

FIG. 1 is a side view of a first embodiment of the present invention, where the whole of sampling apparatus 10 is generally depicted. Sampling apparatus 10 includes a water collection scoop 12 that is attached to hull 14 of vessel 16 with a special through-hull fitting 18. Water collection scoop 12 is mounted to the outside of fitting 18 and, in its preferred embodiment, is positioned on hull 14 so that the water intake is approximately 5 feet below surface 30 of the water. Also, scoop 12 is strategically positioned at a point on the forward portion of hull 14 to minimize cavitation, bubble intake, and any possible contamination of the water stream.

Water inlet piping 20 leads from the outside of scoop 12 through through-hull fitting 18 and into instrument module 22. Instrument module 22 is connected via wires 24 to computer module 26, which, in turn, is connected to the electrical system of vessel 16. It should be understood from the drawings that only scoop 12 is exterior to hull 14. The remaining components are disposed on the interior of hull 14 to increase significantly their operational lifetime.

Computer module 26 contains most of the electronics for sampling apparatus 10. Because it is separated from instrument module 22, it does not contact with the water to be tested. Instrument module 22 contains pipes and sensors for measuring the characteristics of the water that are of interest.

The two modules are separable from one another for ease of placement within the engine rooms or other hold compartments of yachts and other vessels 16. In addition, separation of the electronic components and computer (in computer module 26) from fluid handling and sensing modules in instrument module 22 provides for greater functionality as well as improved safety.

Figure 2:
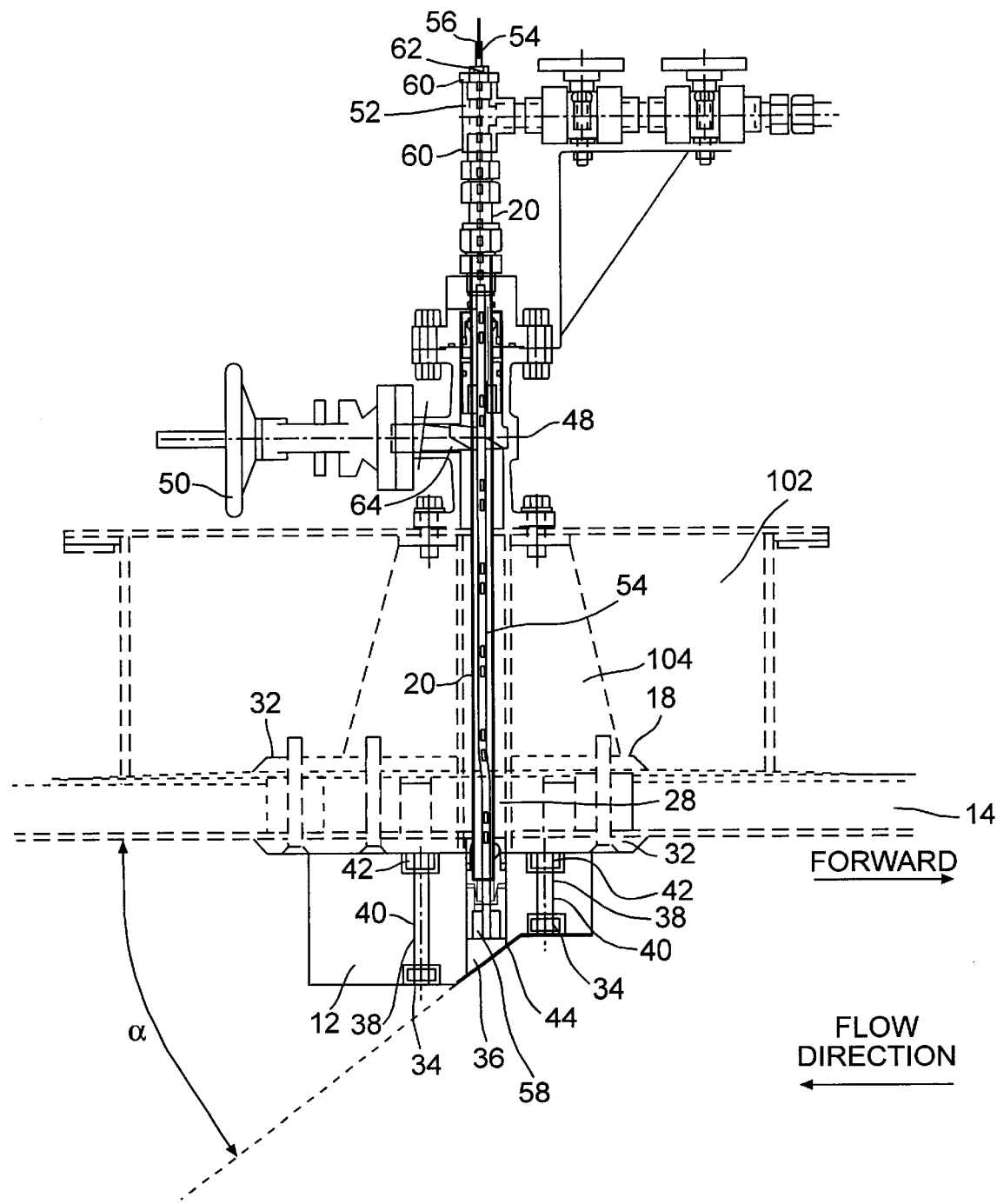
FIG. 2 is a cross-sectional, close-up view of a portion of the present invention, illustrating the design of a first embodiment of the scoop, inlet piping, and valving therefor.

As illustrated in FIGS. 1 and 2, a hole 28 is drilled through hull 14 for passage of inlet piping 20 between instrument module 22 and scoop 12. Whether hull 14 is made from steel, aluminum, fiberglass, composite material, or other suitable material, hole 28 is positioned at a suitable location below the surface of the water 30 (see FIG. 1) to take an appropriate water sample. As mentioned, it is preferred that the sampling point be about 5 feet below surface 30 of the water.

As illustrated in FIG. 2, reinforcing members 32 are attached to the inside and outside of hull 14 around hole 28. Reinforcing members 32 are not required for every installation of sampling apparatus 10, but they are preferred when hull 14 is made of fiberglass. In addition, while reinforcing members 32 are preferably made from aluminum or stainless steel, any other suitable material may be substituted therefor.

On vessels with hulls 14 made of fiberglass, a water tight cofferdam 102 may be built around the through hull fitting 18 unless the through hull fitting 18 is located in a water tight compartment of the vessel already.

Through-hull fitting 18 is positioned as far forward along the hull 14 as possible to minimize cavitation, bubble intake, and any possible contamination of the sampled water stream by the flow of water past hull 14. Preferably, two threaded turrets 42 are welded to reinforcing member 32 on the outside of hull 14.

Figure 3:
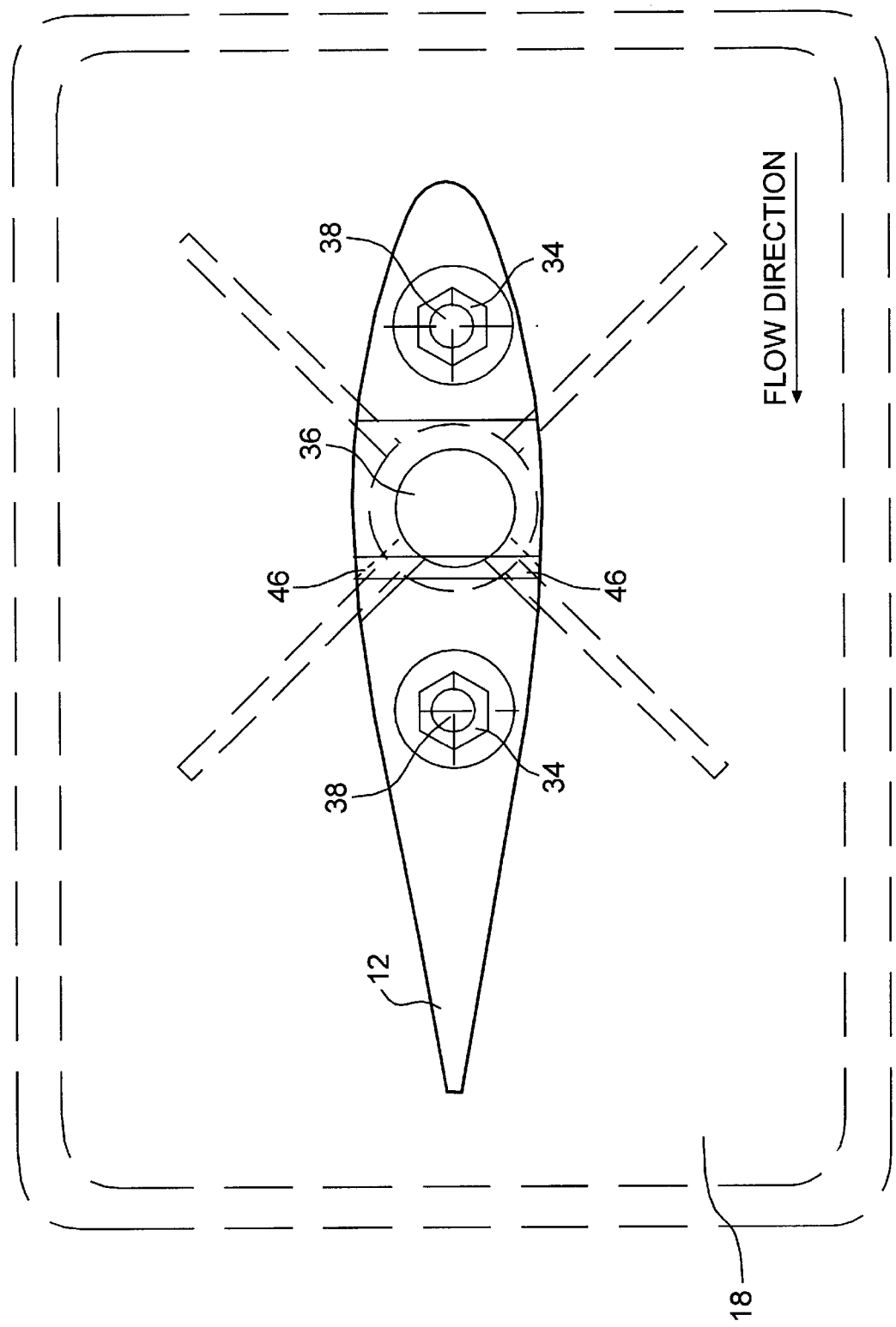
FIG. 3 is a bottom plan view of the present invention as illustrated in FIG. 2, showing the profile of the first embodiment of the scoop.

FIGS. 1, 2, and 3 illustrate a first embodiment of a portion of sampling apparatus 10 of the present invention. As illustrated, water collection scoop 12, which is used with each embodiment (albeit in slightly different arrangements), is described with reference to FIGS. 2 and 3. Scoop 12 protrudes from the bottom or side of hull 14 into the free unperturbed water off the ship's hull. This reduces the inclusion of debris and bubbles from the sampled water that are usually associated with the surface of hull 14. As shown in FIG. 3, scoop 12 is hydrodynamically shaped so that it cuts through the water without creating significant drag or turbulence. Accordingly, water entering scoop inlet 36 contains as little bubbles and/or contamination as possible.

Scoop 12 is designed to break away from vessel or yacht 16 to avoid damage to the hull 14 if excessive force is exerted on scoop 12 (when scoop 12 hits an obstruction, for example). To effect the break away feature, scoop 12 is preferably mounted to through-hull fitting 18, via two "break away" bolts 38, which are threaded through clearance holes 40 of scoop 12 and into threaded turrets 42, which are attached to through-hull fitting 18. When excessive force is exerted, bolts 38 break, and scoop 12 falls away from hull 14, thus minimizing damage to hull 14. The simple attachment of scoop 12 also makes it possible for a diver to easily replace scoop 12 while vessel 16 is in the water.

In the preferred embodiment of the present invention, break away bolts 38 are made from a plastic material so that they are easily broken upon application of sufficient force. It should be noted, however, that break away bolts 38 may be made from any suitable material that shears upon application of sufficient force. In addition, while it is preferred that threaded turrets 42 be welded to through-hull fitting 18, threaded turrets 42 may be attached to through-hull fitting 18 by any suitable, alternative means.

Scoop inlet 36 contains a sieve 44, which is preferably mounted at an approximate 45 degree angle ($\alpha$) to the hull plane with the long axis of scoop 12 parallel to the water streamlines along hull 14. This orientation of scoop inlet 36 creates a shear when ship 16 is underway that reduces snagging or plugging of inlet 36 by large debris. It should be noted that, while a 45 degree angle has been selected for the preferred embodiment of the invention, those skilled in the art could select any of an infinite number of possible angles without deviating from the scope and spirit of the present invention.

Inlet sieve 44 and flow compensation exit ports 46 help to compensate for pressure variations associated with the motion of vessel 16 through the water, as illustrated in FIG. 3. In the preferred embodiment, a single port 46 is located on each side of scoop 12 and extends from the entrance of inlet piping 20 outward and backward (with respect to the forward direction of yacht 16) so that excess water is vented through ports 46.

Figure 4:
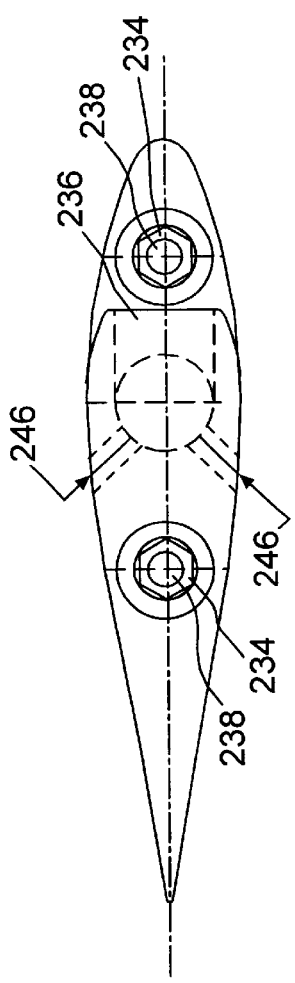
FIG. 4 is a bottom plan view illustration of a second embodiment of the scoop of the present invention.
Figure 5:
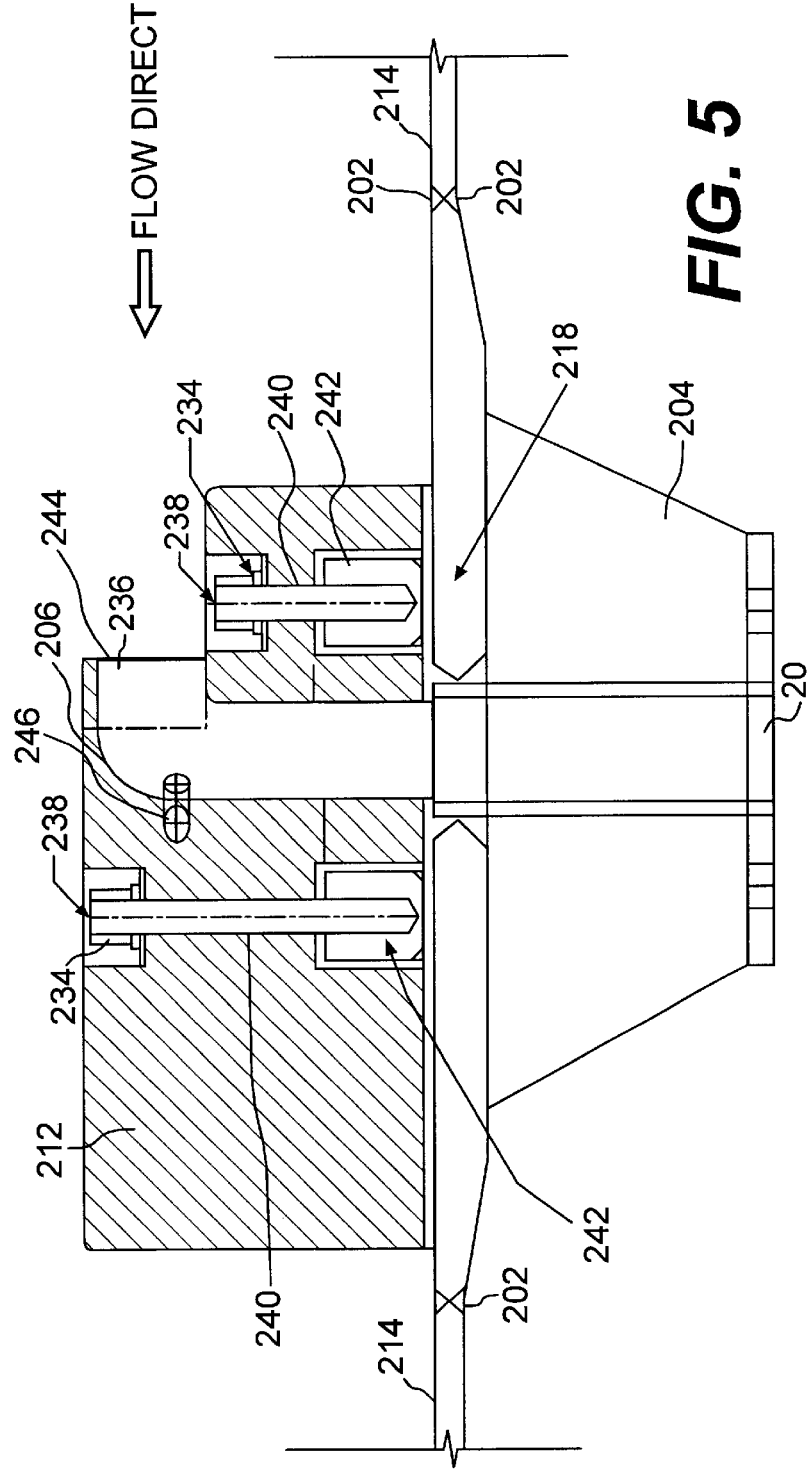
FIG. 5 is a cross-sectional side view of the scoop illustrated in FIG. 4.
Figure 6:
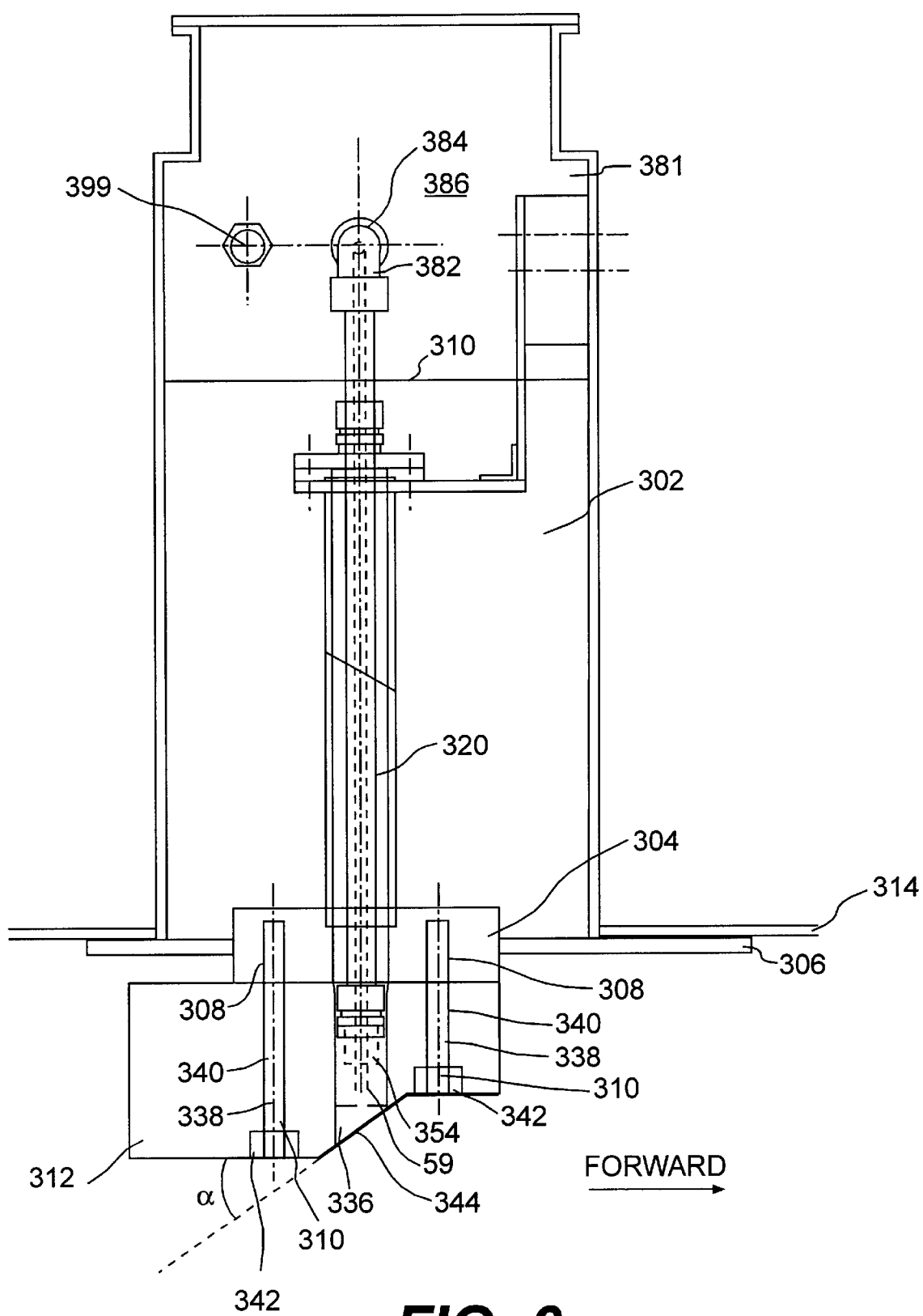
FIG. 6 is a cross-sectional side illustration of a third embodiment of the present invention, where the scoop and inlet piping are installed onto a sea-going vessel through a trunk sea chest.

FIGS. 4 and 5 illustrate a second embodiment of a scoop 212 according to the teachings of the present invention. The second embodiment is similar to the first embodiment, with a few exceptions. First, inlet 236 is not angled at 45 degrees. Instead, inlet 236 faces toward the bow of the vessel 16. Second, hull 214 is made of steel or aluminum, instead of fiberglass. Accordingly, a slightly different through-hull fitting 218 is required. In this embodiment, insert plate 218 replaces through-hull fitting 18 (of the first embodiment) and is welded into the hull 214 at weld points 202. Gusset plate 204 is connected to insert plate 218 on the inside of hull 214. As in the first embodiment, threaded turrets 242 are welded to the outside of insert plate 218.

As with the first embodiment, scoop 212 is connected to hull 214 by break away bolts 238 that are inserted into threaded turrets 242 that are welded (preferably) to the outside surface of insert plate 218 Nuts 234 at the top of bolts 238 hold scoop 212 onto hull 214. If excessive force is applied to scoop 212 while vessel 216 is underway, break-away bolts 238 will shear off and scoop 212 will fall away from hull 214 to minimize damage thereto.

As with the first embodiment, scoop 212 preferably is provided with flow compensation exit ports 246, as shown in FIG. 4, that help to reduce the pressure on scoop 212 by permitting excess water to flow back into the water body from inlet 236 of scoop 212. In addition, sieve 244 may be provided over the end of inlet 236 to minimize the ingestion of large particles by inlet 236.

FIGS. 6, 7, 8, 9, and 10 illustrate a third embodiment of the present invention, which is similar to the first two embodiments, except that scoop 312 is mounted to yacht 16 through a trunk sea chest 302 in hull 314, instead of through through-hull fitting 18. Mounting block 304, which is made of aluminum or any other suitable material, is securely welded into a hole cut in grate 306 of trunk sea chest 302. As shown in FIG. 10, mounting block 304 has contours that complement the contours of scoop 312. Blind threaded holes 340 in mounting block 304 are designed to accommodate break away bolts 338 for mounting scoop 312 to mounting block 304. Water inlet piping 320 passes through scoop 312 and mounting block 304, and extends into trunk sea chest 302.

As with the first embodiment, scoop 312 may be provided with a sieve 344 that extends over inlet 336. As with the previous embodiments, break-away bolts 338 attach to mounting block 304. If excessive force is exerted on scoop 312 during use, break-away bolts 338 shear off and permit scoop 312 to detach from mounting block 304 to minimize any damage to grate 306 or to hull 314. As with the first embodiment, break away bolts 338 may be made from plastic or any other suitable material.

Figure 12:
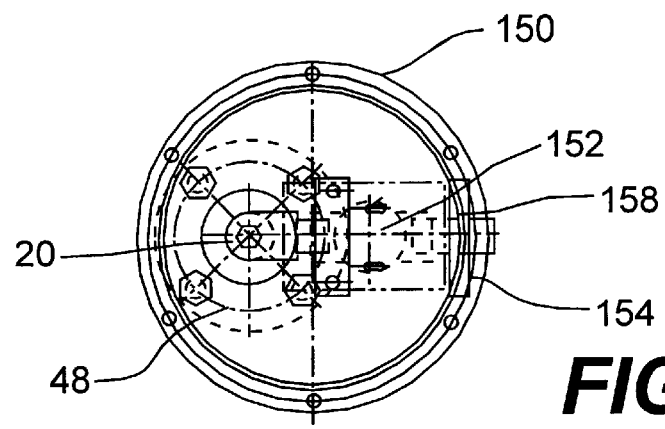
FIG. 12 is a top plan view illustration of the containment vessel incorporated in the embodiment of the present invention shown in FIG. 11.
Figure 11:
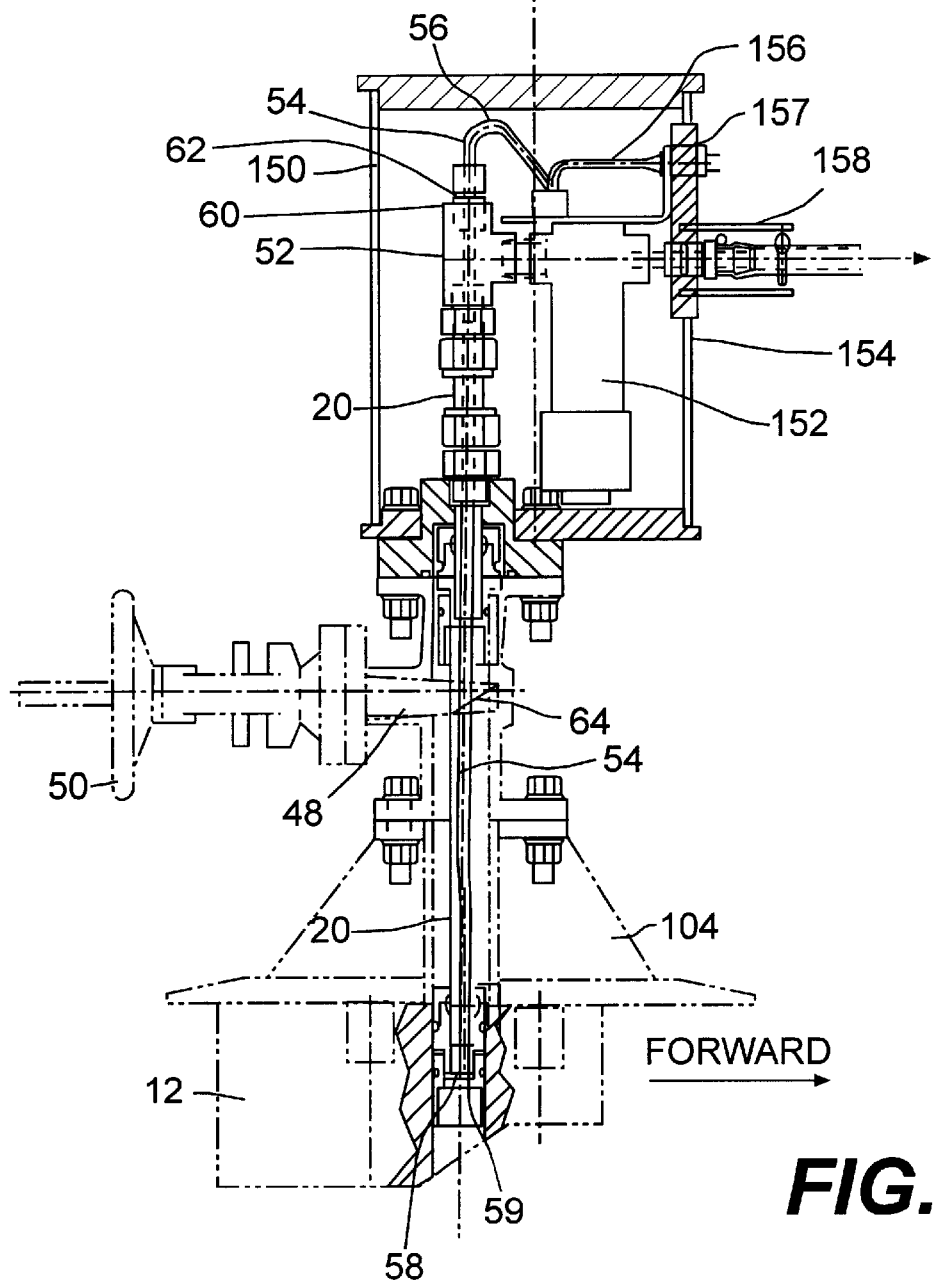
FIG. 11 is a side view illustration of a fourth embodiment of the scoop and inlet piping of the present invention, showing the addition of a containment vessel.

FIGS. 11 and 12 illustrate the fourth embodiment of the present invention. Here, the design and construction of scoop 12 and much of inlet piping 20 is the same as for the first embodiment illustrated in FIG. 2. In this embodiment, however, a containment vessel 150 and automatic shut off valve 158 have been added to the design adjacent to sharpened gate valve 48. Should a leak develop in inlet piping 20 that extends in the downstream direction from valve 48, containment vessel 150 prevents water from entering vessel 16.

Water is pumped from inlet piping 20 through T-fitting 62. From T-fitting 62, the water travels through solenoid valve 152, which is also positioned within containment vessel 150. The water exits through a side wall 154 of containment vessel 150. From containment vessel 150, the water proceeds to instrument module 22 for analysis. Wires 156 extend into containment vessel 150 to provide an actuating signal or power to solenoid valve 152.

To prevent ingress of water into vessel 16, a water sensor (not shown) is provided in instrument module 22. If water is detected in instrument module 22, a signal is sent to solenoid valve 152 to close inlet piping 20 to prevent further ingress of water into vessel 16. At the same time, a separate signal is sent to pump 510 to shut it down. The water sensor in instrument module 22 is positioned specifically to detect water in the cabinet, regardless of the location of the leak. For example, the water sensor may be positioned at the bottom of the cabinet 22.

In the embodiment illustrated in FIG. 11, all internal plumbing is preferably made from stainless steel reinforced ⅝ inch Teflon® (polytetrafluoroethylene or PTFE) tubing, which is fully strain relieved at both containment vessel 150 and instrument module 22 and the overside discharge.

Containment vessel 150 is preferably made from a sturdy 16 gauge stainless steel cylinder and is preferably mounted atop sharpened gate valve 48. All pass-through holes in the embodiment are preferably sealed with o-rings or other suitable sealing means. Preferably, electrical leads 156 pass through a sealed, water-tight connector 157 disposed through side wall 154 of containment vessel 150.

Water inlet piping 20 according to a first embodiment will now be described with reference to the particular arrangement illustrated in FIG. 2. Inlet piping 20 leads from inlet sieve 44, through through-hull fitting 18, into the inside of yacht 16. Inlet piping passes through or adjacent to a gusset plate 104 that may be attached to the interior surface of through-hull fitting 18. Inlet piping 20 may also pass through a cofferdam 102, if included on the particular vessel 16.

Upon exiting the cofferdam 102 (FIG. 2) on fiber glass hulled vessels, or upon entering vessel 16 with other than fiberglass hulls (FIG. 11), inlet piping 20 is connected to a sharpened gate valve 48, which is shown as a gate valve with a manually-operated hand wheel 50. Sharpened gate valve 48 prevents the flow of water from entering vessel 16, should scoop 12 or inlet piping 20 become damaged during operation. Sharpened gate valve 48 permits the operator of vessel 16 to seal off hole 28 through hull 14, if necessary. Preferably, the sharpened gate valve 48 is a stainless steel guillotine gate valve. However, as would be understood by those skilled in the art, there are many suitable alternatives to the sharpened gate valve 48 that may be used without deviating from the scope and spirit of the present invention.

From sharpened gate valve 48, inlet piping 20 continues along a straight line to T-fitting 52. The portion of inlet piping 20 that extends to T-fitting 52 acts as a conduit for a probe 54 that extends from a point 56 (ee FIG. 2) at the exterior of inlet piping 20 to a point just inside of inlet 36 where a probe tip 58 is positioned. Probe tip 58 preferably includes a temperature sensor thereon so that accurate temperature data is assured. If temperature sensor were located within vessel 16, the interior temperature of vessel 16 might adversely affect the temperature reading.

Inlet piping 20 leads into one of two openings 60 of T-fitting 52. Probe adapter 62 is attached to the other top opening 60. Probe 54 is fed through adapter 62 and inlet piping 20 until its out of vessel 16 and the probe end 58 reaches inlet 36 of scoop 12 just behind inlet sieve 44, which acts as a positive stop. In the preferred embodiment, probe 54 comprises a Teflon® hose (containing wiring), a temperature sensor at the outside of vessel end 58, and an anti-fouling and calibration electrode array 59. Probe 54, however, need not be limited to any particular sensor or group of sensors. Additional sensors can be added to probe 54 without deviating from the scope of the present invention, as would be understood by those skilled in the art.

Because probe 54 extends from inlet 36 through inlet piping 20 to probe adapter 62, probe 54 can be easily removed for maintenance, replacement, or upgrading by extracting it with pipe 20 through the modified stainless steel gate (cut-off) valve 48, closing modified gate valve 48 and then removing the probe through adapter 62. Probe 54 can be returned to operation by simply reversing this process. The proper positioning of probe end 58 in inlet 36 is determined by using sieve 44 as a positive stop.

If required during an emergency, the crank 50 of gate valve 48 can be closed while probe 54 is installed in inlet piping 20. A guillotine portion 64 of the modified gate valve 48 simply cuts through probe 54 and closes off the flow of water in inlet piping 20 and sensor piping 54.

While not illustrated in FIGS. 4 or 5, the same inlet piping arrangement 20 (as illustrated for the first embodiment) may be used in the second embodiment of the present invention. If so, after gusset plate 204, inlet piping arrangement 20 will mirror the construction shown in FIG. 2. In this embodiment, however, the placement of probe tip is not determined by sieve 244. Instead, bend 206 in inlet piping 20, just inside of inlet 236, acts as the positive stop for the probe tip (not shown).

The third embodiment of a portion of the present invention is illustrated in FIGS. 6–10. Here, scoop 312 is attached to mounting block 304, which is attached to grate 306 on trunk sea chest 302. In the embodiment shown, trunk sea chest 302 is vertically oriented, which means that scoop 312 faces forward from the bottom of hull 314. Grate 306, which includes holes 308 therethrough that permits water to fill trunk sea chest 302 to water line 380, is positioned at the bottom of trunk sea chest 302. An air pocket 381 is present above water line 380 within trunk sea chest 302. In fact, the trunk sea chest 302 is defined as a sea chest which is also a trunk rising above the water line inside the vessel 16.

Inlet piping 320 extends from inlet 336 up to elbow 382. From elbow 382, which changes the direction of inlet piping 320 ninety degrees, inlet piping passes 320 through a gland sealed hole 384 in side wall 386 of trunk sea chest 302 and into the interior of vessel 16. Inlet piping 320 continues from the gland sealed hole 384 to a T-fitting 388, where the direction of the water flow is changed another ninety degrees. At an end 390 of T-fitting 388, an adapter 392 is fitted. The electrical leads 394 that are connected to probe 354 pass through adapter 392. From fitting 388, water flows through a ball valve 396 before entering instrument module 22, a portion of which is illustrated in FIG. 7.

As with the first embodiment of the present invention, the construction of inlet piping 320 permits an easy removal and installation of probe 354. As with the first embodiment, after removal of adapter 392, probe 354 may be extracted with inlet piping 320 through the top of the trunk sea chest, after disconnecting elbow 382 from horizontal pipe 320 and drawing the wiring end of the probe 354 through the horizontal pipe 320. To install a new probe into inlet piping 320, one needs only to reverse the above described process.

Water drawn through piping 320 then proceeds to instrument module 22, where characteristics of the water are measured. After being analyzed in instrument module 22, the water is returned to the interior of trunk sea chest 302 via outlet piping 391. Before entering trunk sea chest 302, the water passes through a ball valve 393, an elbow 395, a fitting 397 that passes thorough a gland sealed hole 398 in wall 386 of trunk sea chest, and finally to outlet 399 where the water is discharged into the trunk sea chest 302. From trunk sea chest 302, the water may exit through grate 306 and return to the open sea.

Figure 9:
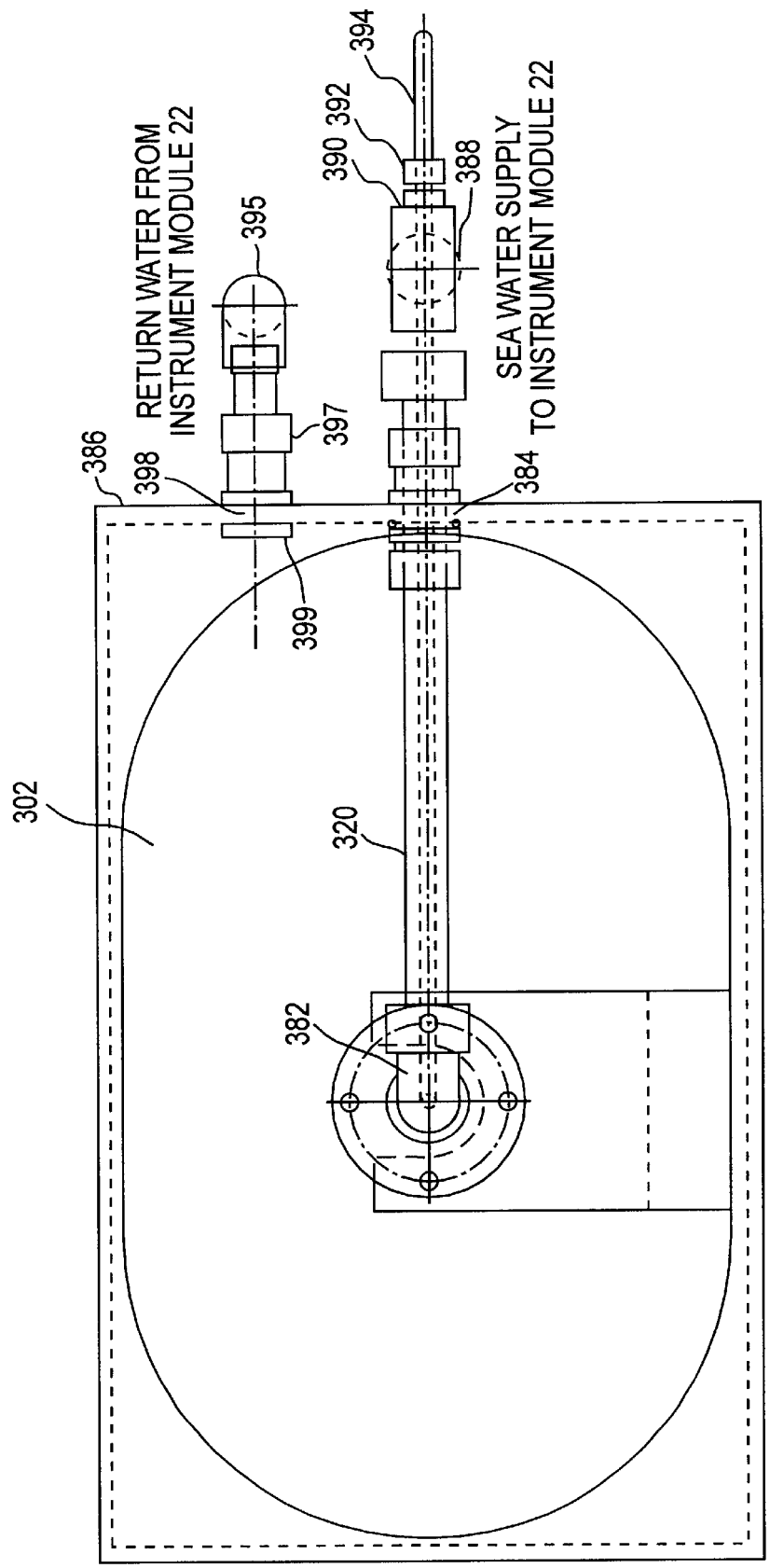
FIG. 9 is a top plan view of the embodiment of the present invention illustrated in FIGS. 6–8, showing the preferred positioning of the inlet and return piping in relation to the trunk sea chest.

FIG. 9 illustrates a top plan view of trunk sea chest 302, showing the positions of inlet piping 320 and water return 399 for the third embodiment. As illustrated, inlet piping 320 and water return piping 391 preferably lie side-by-side in trunk sea chest 302.

Figure 13:
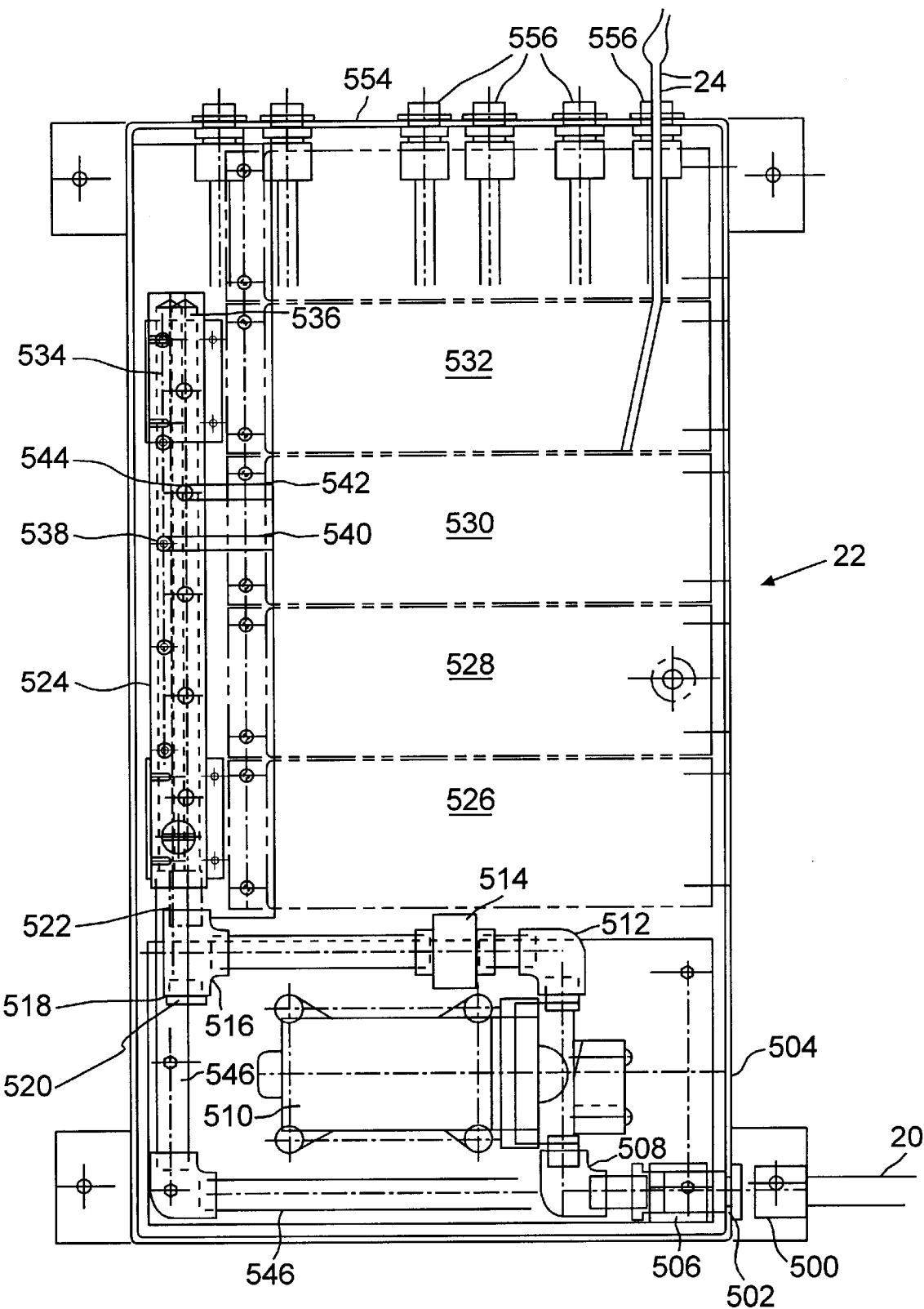
FIG. 13 is a front view of the layout of components within the instrument module of the present invention.
Figure 14:
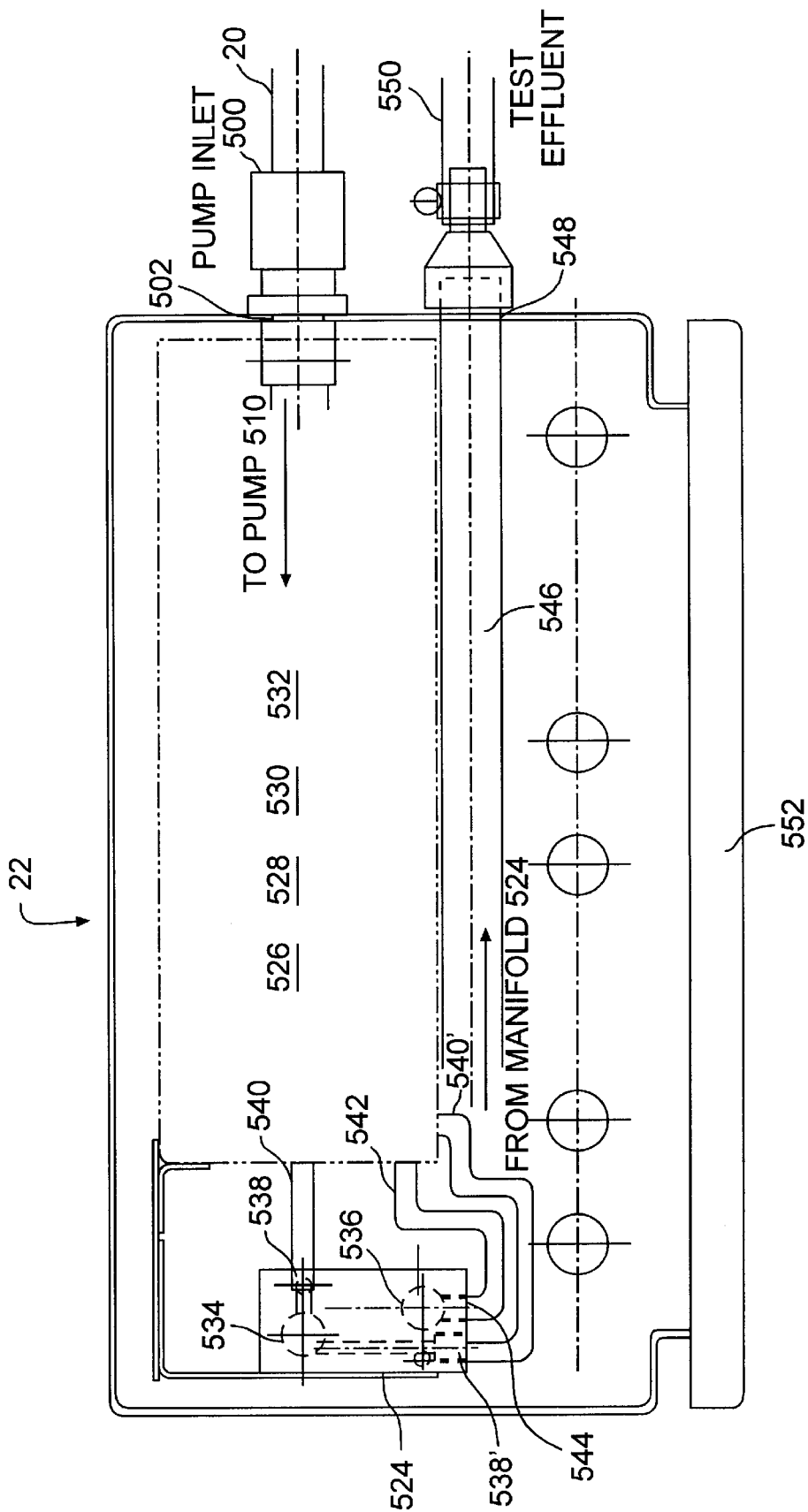
FIG. 14 is a top plan view of the layout of components in the instrument module illustrated in FIG. 13.
Figure 15:
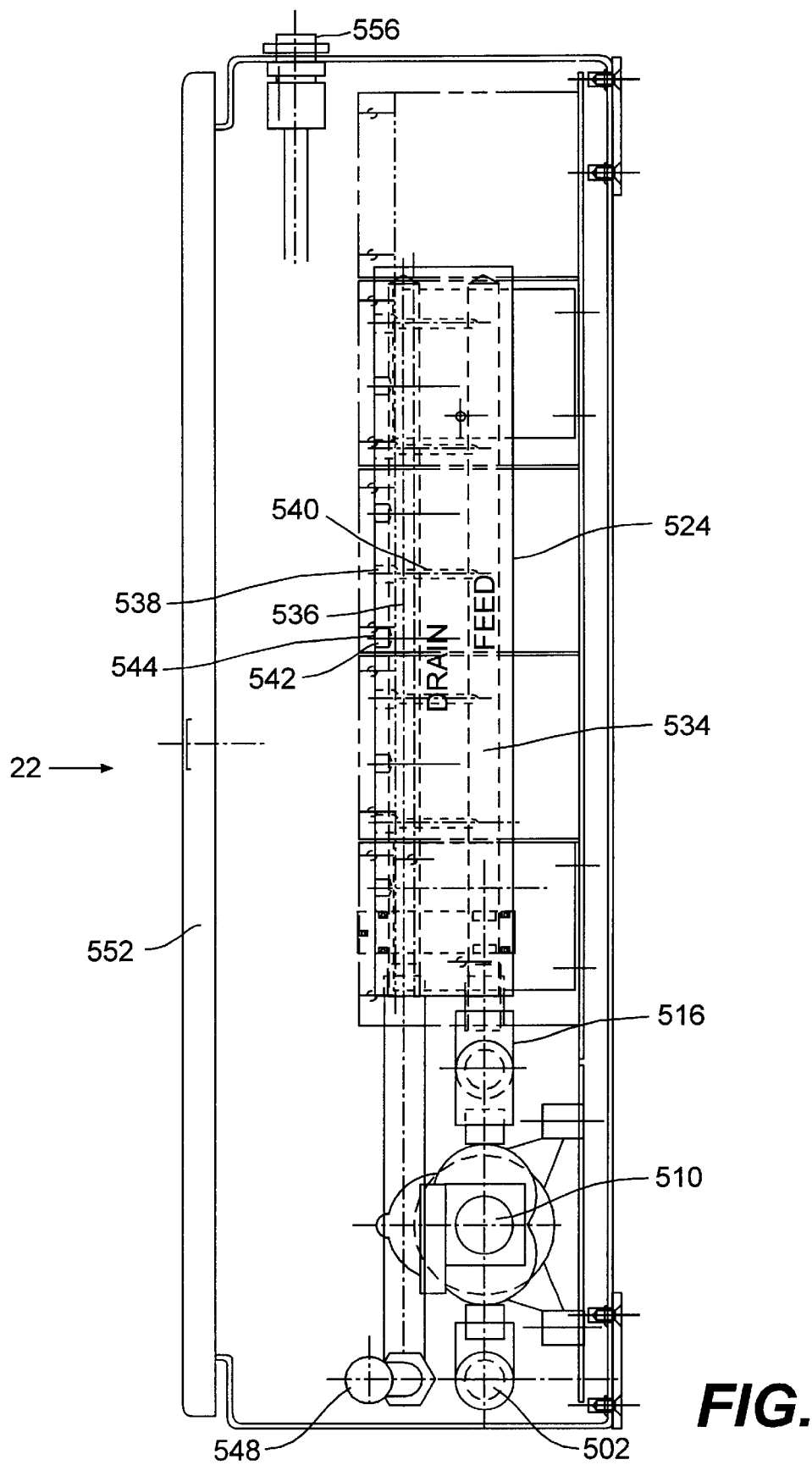
FIG. 15 is a side view of the layout of components in the instrument module illustrated in FIGS. 13 and 14.

FIG. 13 is a front view illustration of the basic layout for instrument module 22. As illustrated, inlet piping 20 from scoop 12 (or from scoop 212 or 312, depending on the embodiment installed on vessel 16) enters instrument module 22 through fitting 500 at the exterior of cabinet 22. From fitting 500, the water passes through a hole 502 in wall 504 of cabinet 22. Once inside of cabinet 22, the water passes through a bushing 506 and an elbow 508 before entering water pump 510. In the preferred embodiment of instrument module 22, pump 510 is a Shurflo 414® pump. However, as would be understood by those skilled in the art, any suitable water pump may be substituted therefor.

Figure 21:
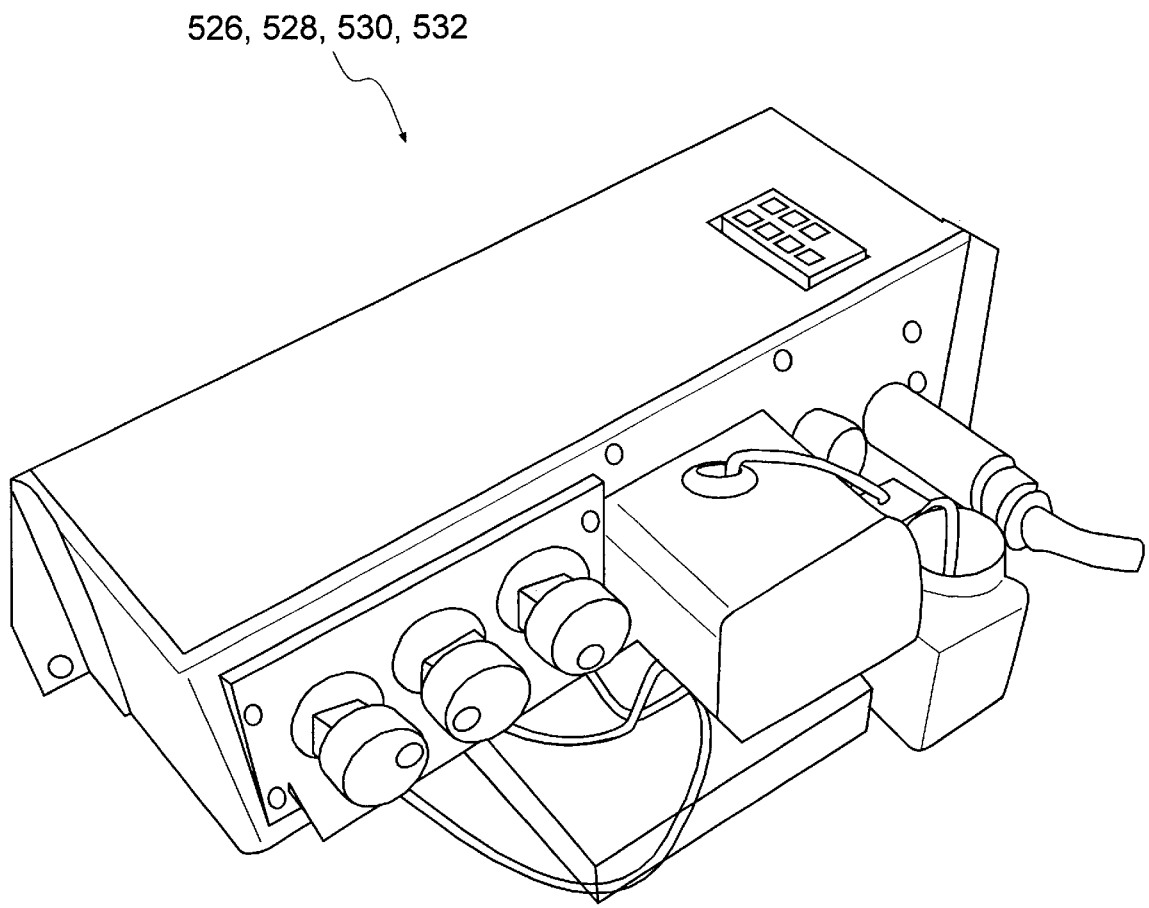
FIG. 21 is a perspective illustration of a representative testing unit, specifically a dissolved $CO_2$ measuring unit, that may be used in the instrument module of the present invention.

From pump 510, the water passes through an elbow 512, a union 514, and a T-fitting 516. T-fitting 516 is closed at end 518 by plug 520. The other end 522 of T-fitting 516 is open and permits the water to flow into manifold 524 where it is distributed to the various testing equipment 526, 528, 530, and 532 in instrument module 22. Each testing unit (submodule) 526, 528, 530, 532 performs a test or multiple tests on the water to measure particular parameters about the water. As mentioned above, the parameters include: temperature, salinity, oxygen, pH, redox, optical (beam attenuation and ocean color) and bio-optical parameters (e.g., Chlorophyll a), toxic heavy metals, $CO_2$ content, and other biological and chemical and physical characteristics, among others. FIG. 21 illustrates one such testing module 526, 528, 530, 532. Specifically, the testing module illustrated is a dissolved $CO_2$ measuring unit that may be provided in instrument cabinet 22.

As illustrated in FIG. 13, testing units 526, 528, 530, 532 are connected in parallel to manifold 524. This parallel connection is beneficial because some of the testing units introduce chemical reactants into the water while measuring characteristics of the water. To prevent the reactants from different testing units from interacting with one another, the testing units are connected in parallel to manifold 524. Of course, where they will not interfere with the operation of other testing units, some testing units may be connected in series with one another. The exact arrangement of the testing units may differ from vessel to vessel depending upon the data that the particular sampling apparatus 10 is designed to collect.

In FIG. 13, while only four testing units 526, 528, 530, 532 are illustrated, it should be noted that any number of testing units may be incorporated into instrument module 22 and that the total number is not limited to four. Moreover, the individual testing units preferably are plug-in units, which means that they may be plugged into instrument module 22 at any suitable location. Since they are plug-in units, the testing units may be easily removed and replaced at the end of their useful lifetimes or upon failure of the unit.

Figure 20:
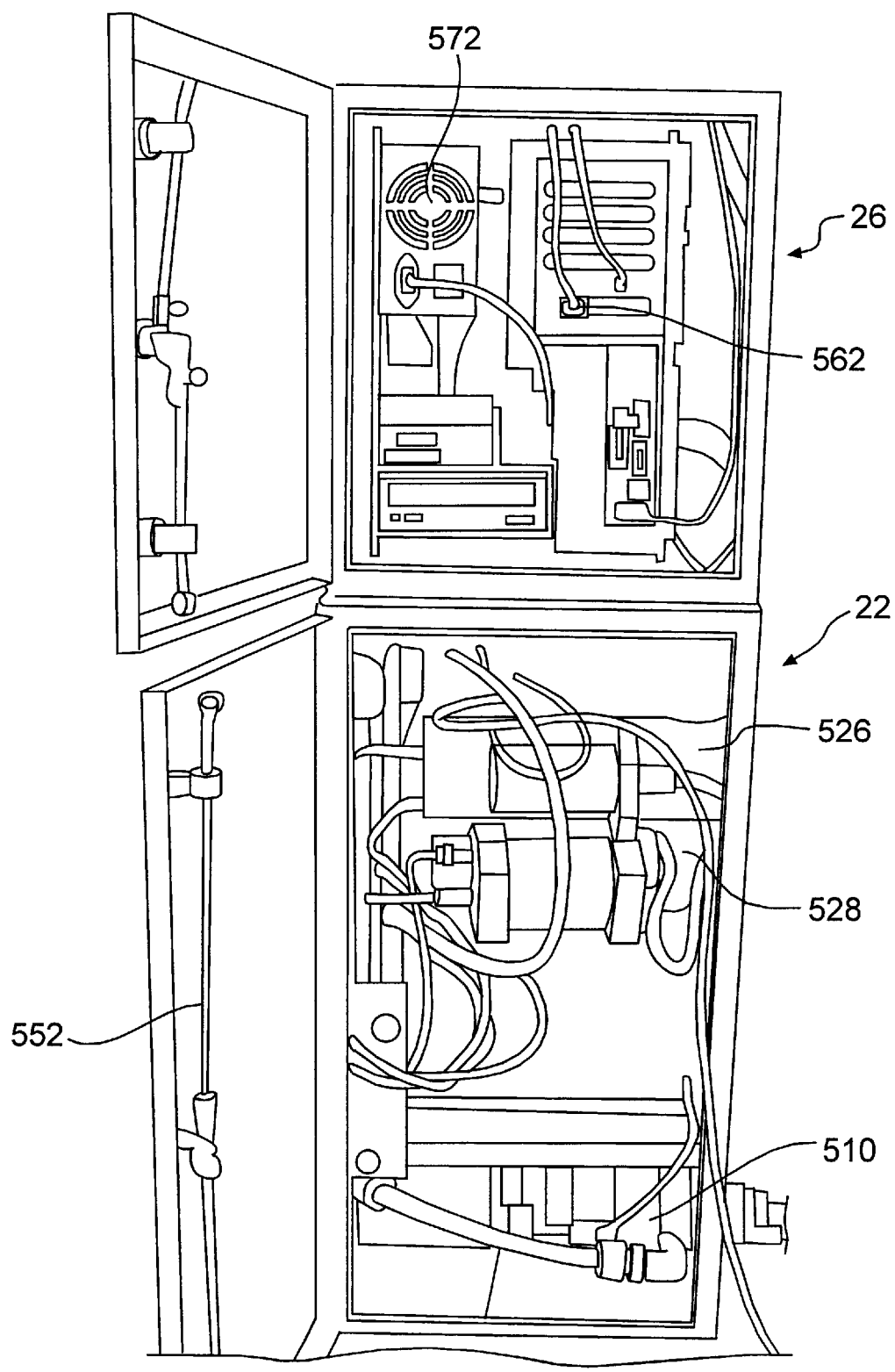
FIG. 20 is a front view illustration of the instrument module and the computer module of the present invention.

In its preferred embodiment, the various testing units, submodules, or sensors expected to be used with sampling apparatus 10 are expected to be "off the shelf" components appropriately modified to fit in the instrument module 22 and to operate off of apparatus 10's standard power, light, anti-biofouling, calibration and software systems. In other words, it is expected that various sensors will be manufactured by companies that specialize in the design and manufacture of those components and adapted to meet apparatus 10's standards. The instrument module 22 is designed to have sensors deployed in submodules (526–532) that can be shipped (mailed) to wherever apparatus 10 is located and simply snapped into place. The submodules with their sensors can also be easily removed (snapped out) of apparatus 10 and sent back to their manufacturer for cleaning, servicing or recalibration. Testing apparatus 10, therefore, serves as a "research platform" that can house multiple interchangeable sensors depending upon the water characteristics to be sampled in any part of the world. A detailed view of computer module 26 and instrument module 22 is illustrated in FIG. 20.

Preferably, sampling apparatus 10 is equipped to provide the following standard measurements: true water temperature (as measured external to the ship's hull), internal module water temperature, pressure, salinity (as calculated from measured conductivity, temperature and pressure), dissolved oxygen gas, pH, Eh, and Chlorophyll (as measured by fluorescence). In addition, sampling apparatus 10 may include testing units that measure turbidity and optical attenuation of near-ultraviolet and visible wavelengths in water. In addition, sampling apparatus 10 may be provided with measurement capabilities including bioluminescence, nutrients (i.e., nitrate, phosphate, silicate and ammonia), environmentally hazardous metals (i.e., copper, zinc, lead, cadmium, iron, manganese, and HS—), dissolved carbon dioxide, and assays for materials such as algal biotoxins and other organic compounds.

Aside from these in-water measurements, sampling apparatus 10 may also be provided with other sensors that measure ambient atmospheric conditions such as: air temperature, barometric pressure, humidity, wind speed and direction, and solar radiation. In addition, sampling apparatus 10 may measure other atmospheric parameters including: ozone concentration, carbon monoxide concentration, and atmospheric aerosol optical depth.

Table I lists the various types of readings that may be recorded by sampling apparatus 10 along with a brief description of the method utilized to make the measurements.

TABLE I

| SENSOR | METHOD OF MEASUREMENT |
| --- | --- |
| Salinity | Calculated from Conductivity, Temperature and Pressure |
| Water Temperature | Platinum resistance thermometer |
| Dissolved Oxygen | Clark Electrode |
| pH | pH electrode |
| Eh | Eh electrode |
| Chlorophyll | Fluorescence |

TABLE I-continued

| SENSOR | METHOD OF MEASUREMENT |
| --- | --- |
| CDOM | Fluorescence |
| Turbidity | Nephelometry |
| Meteorological observations: | Standard Weather Package: |
| Wind Speed and Direction | Vane anemometer with magnetic compass, |
| Atmospheric Pressure | Electronic barometer with a Gill pressure port to minimize dynamic errors |
| Atmospheric Temperature | Platinum resistance thermometer |
| Relative Humidity | Vaisala intercap both temperature and humidity sensors are mounted within a Gill multiplated radiation shield. |
| GPS | Commercial GPS |
| Bioluminescence | Luminometry |
| Toxic metals | Anodic Stripping Voltametry |
| Phosphate | Colorimetric Flow Analysis |
| Silicate | Colorimetric Flow Analysis |
| $pCO_2$ | Non-dispersive Infared Detector |
| Biochemical | "Chemistry on a Chip" Sensors |
| Ozone | Non-Dispersive Infared Detector |
| Solar radiation | Radiometer |

In reality, an unlimited number of sensors could be developed to work within the sampling apparatus 10 and, as a result, Table I is not meant to limit the scope of the present invention. Instead, the sensors (testing units) listed in Table I are meant to be examples of the type and quantity of sensors that can be incorporated into sampling apparatus 10. The overall concept behind the design of sampling apparatus 10 is that any company, individual, government agency, etc., may develop and deploy a unique sensor (or group of sensors) depending upon the data to be collected.

Regardless of who provides a particular sensor for apparatus 10, each sensor must be compatible with the module's standardized and integrated software, power and light sources, calibration systems, anti-fouling systems and sampling techniques. And these sensors must be embodied in a submodule that can be plugged into one or more of the modular spaces in the instrument module 22, 526–532.

As illustrated in FIGS. 11–13, manifold 524 has a water supply conduit 534 and a water return conduit 536 incorporated therein. Water flowing through water supply conduit 534 from pump 510 exits from supply conduit 534 through a supply hole 538 and passes through a supply line 540 to the test unit (in this case 530, as shown in FIG. 13). After being tested, the water flows through a return line 542 to a return opening 544 in return conduit 536. The water from each of the testing units is returned to return conduit 536, where it flows through return piping 546, out of instrument module 22, through outlet 548, into outlet piping 550, and eventually back to the body of water from which it was drawn. A door 552 provides access to the interior of instrument module 22.

In an alternative embodiment of the invention, the instrument module 22, water manifold 524 is connected to a below water level intake line which allows water to be pumped through inert (Teflon®) tubing with an impeller pump. The water manifold design, consisting of a single block (of PTFE, PVDF, with a tradename "KYNAR", or other inert material) and installed plumbing, allows for the flow of a seawater stream into each of up to five separate sensor sub-modules (or more), each capable of having its own flow cell or sample interaction zone, and its own watertight electronics and signal conditioning compartment. Data from the individual sensor modules is interfaced to common computer system 562, either through direct analog to digital converter data acquisition or through embedded microprocessors. A common drainage system passes the flowing seawater back to the exterior, typically (on vessels) through the ship's own waste water system. All sensor sub-modules 526, 528, 530, 532 operate off the same power and light sources and utilize the same anti-fouling, calibration, and software systems.

Preferably, the instrument module and computer module are both approx. 16" wide and 9.5" deep. Computer module 26 preferably is 18" high and instrument module 22 preferably is 30" high. The relative position of the fluidics module's pump 510, seawater plumbing system and computer system 562 are shown as are sensor boxes, connected to the common intake manifold 524.

Positioning and operating sampling apparatus 10 essentially out of the water, whether positioned in private yachts or other vessels 16, on other forms of sea or lake platforms, or on the docks of aquaculture facilities or fresh water reservoirs, ensures that the various components (including the sensors and probes) of sampling apparatus 10 will interact minimally with ocean or other water carrying surface fouling materials. Because of this, and because of the sophisticated automated anti-fouling procedures described in greater detail below, sampling apparatus 10 requires far less cleaning than buoys, drifters, or other unattended systems deployed in oceans or other bodies of water. Moreover, because of its modular design, the individual testing units 526, 528, 530, 532 within sampling apparatus 10 may be easily and periodically removed, cleaned, and replaced.

One of the most perplexing problems associated with long-term unattended measurements in natural waters, and particularly in seawater, is bio-fouling, which occurs on system surfaces after extended submersion in water. As fouling progresses, the operating characteristics and calibration of the sensors are altered, eventually to the point where the sensors provide erroneous measurements. In addition, when the population of the organisms occupying the surfaces of the testing systems become high enough, the organisms noticeably modify the characteristics of the water in the flow path to the sensors.

So that sampling apparatus 10 operates autonomously and for long periods of time, an automatic anti-fouling system is incorporated therein. The operation of a preferred embodiment of that anti-fouling system will now be described. It should be recognized, however, that other suitable anti-fouling systems may be incorporated into sampling apparatus 10 without deviating from the scope and spirit of the present invention.

As is known to those skilled in the art, various methods may be used to combat the fouling problem. For example, freshwater may be added to the water covering the wetted parts of sampling apparatus 10 to change the water chemistry enough to kill and wash away living biological contaminants. Also, slowly-dissolving toxic chemicals may be continuously added to the water covering the wetted parts to kill biological organisms and remove them from the system.

In sampling apparatus 10, a number of techniques are integrated together to alleviate the bio-fouling problem. While the particular techniques described below are preferred for sampling apparatus 10, it should be noted that those skilled in the art may substitute other techniques therefor without deviating from the scope and spirit of the present invention.

Adhesion and settling are two bio-fouling problems that are addressed by the design of sampling apparatus 10. Adhesion refers to the growth of biological materials on wetted surfaces within apparatus 10. Settling refers to the accumulation of biological materials in areas within apparatus 10 where water flows slowly or not at all. Settling is particularly pronounced when 510 within instrument module 22 is not operating, when apparatus 10 is turned off, or when apparatus 10 lies dormant, which occurs between sampling cycles. The problem of adhesion is also exaggerated during dormant periods of apparatus 10.

To minimize adhesion and settling, PFA Teflon® is used for as many of the wetted surfaces as feasible. This material makes it difficult for organisms to develop good adhesion. Also, all wetted components in the system are exposed to a toxic chemical wash (e.g., a solution containing sufficient amounts of chemical oxidants probably composed of peroxides and halogen compounds) just before the pump shuts down. If, on the other hand, sampling apparatus 10 operates for long periods of time between shut-downs, the toxic chemical wash is applied at set intervals to prevent bio-fouling problems from developing.

The preferred way in which the anti-fouling system functions is by applying a low voltage (AC or DC) between electrodes 59 at end 58 of the through-hull Teflon probe 54. Inert metals are used for the electrodes 59 to avoid excessive corrosion of the electrodes 59 and metal contamination of the downstream water. It is believed that all metals will work for this application, but specific metals are preferred, as described in greater detail below with respect to the calibration system incorporated into sampling apparatus 10.

The anti-fouling system incorporated into the present invention is automatically operated by computer 562. The operation of the anti-fouling electrodes 59 (which are located at probe tip 58) is initiated by the computer software within computer module 26. The software may be programmed to initiate the anti-fouling procedure either on a regular schedule or intermittently, depending on the operational mode of the overall system and the status of vessel 16 or any of the other buoys, piers, or platforms upon which apparatus 10 is located. A record of the operation and performance characteristics of the anti-fouling system is imbedded in the data record for the Eh sensor since this sensor is linearly responsive to the concentration of the electrochemical products in the water.

At its top 554, instrument module 22 is provided with a number of electrical conduits 556 through which wires 24 pass from testing units 526, 528, 530, 532 to computer module 26. Computer module 26 will now be described in connection with FIG. 16.

Computer module 26 includes a number of electrical conduits 558 through which wires 24 pass from instrument module 22. Computer module 26 also includes a number of conduits 560. Conduits 560 may be used for any number of reasons. For example, conduits 560 may contain the power cables that connect the individual electronic components within computer module 26 to the power supply of vessel 16. Conduits 560 may also permit data cables to exit computer module and connect to satellite or other communications equipment so that data may be transmitted to a remote location. They may also contain electrical connections to other sensors (such as weather sensors or a Global Positioning System) that are not part of the instrument module 22, but which provide data about ambient environmental conditions to computer 562. Conduit 560 may also contain wires that connect to the vessel's computer network so that displays of the data being collected by apparatus 10 can be displayed.

Figure 16:
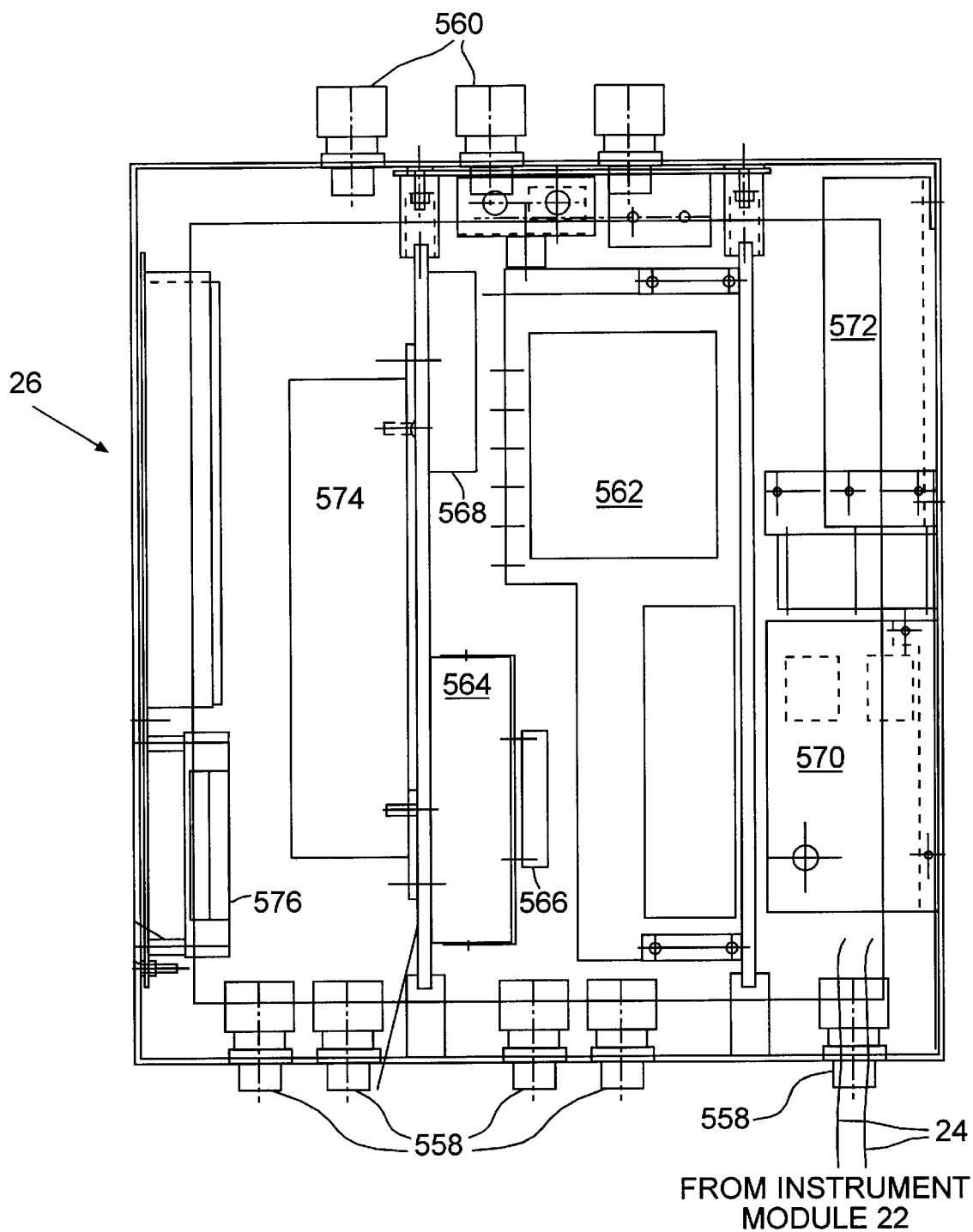
FIG. 16 is a front view of the layout of components in the computer module of the present invention.

As illustrated in FIG. 16, computer module 26 includes the electronic components that are associated with sampling apparatus 10. Computer module 26 also contains the power supply and connections to the power supply for the various elements of sampling apparatus 10.

While there are many different pieces of equipment that may be included in computer module 26, in the preferred embodiment, there is at least a computer (or CPU) 562 capable of receiving electronic signals representative of the data generated by each of the individual testing units 526, 528, 530, 532. Computer 562 may be equipped with a CD ROM 564 for running the various software programs thereon. It may also include a recordable CD (also known as a CD-R) for storing collected data. Computer 562 may also be connected with a hard drive 566, on which the operating software is stored. So that data may be exported on a standard floppy diskette (or alternatively imported from a standard diskette), a 3½ inch disk drive 568 may also be connected to CPU 562.

For the operation of computer module 26, a power supply 570 may be included therein. A heat sink 572 may also be incorporated in computer module 26 as may be the electronic components for a satellite communications system (i.e. INMARSAT C) and a Global Positioning System (GPS) 574. Additionally, computer module 26 may house a relay box 576 which may permit the computer or CPU to control up to 8 external devices like for example pumps, solenoids, electrical toxic chemical generation, etc. Other electronic and electrical equipment may also be included in computer module 26 depending on the amount and type of information collected by sampling apparatus 10.

The connection of the various components within computer module 26 is not laid out in the various drawings because the exact wiring configuration is expected to differ from one embodiment of sampling apparatus to the next. Moreover, the precise manner in which various components are connected would be known to those skilled in the art.

Computer 562 includes software that controls the calibration of testing units 526, 528, 530, 532 within instrument module 22. The calibration procedures and internal check routines ensure proper operation of sampling apparatus 10. There are three primary ways in which calibration of the sensors is accomplished: (1) electro-generation or coulometric generation of chemical agents, which provide surrogate calibration signals for appropriate individual sensors, (2) exchanging in-service testing units (submodules) with calibrated testing units at regular intervals, and (3) packaging of reagent solutions and calibrant solutions within sensing apparatus 10, which can be periodically pumped into wetted sensing zones of individual modules for detection.

It is nearly impossible (or at least highly impractical) to conduct autonomous sampling procedures for many environmental parameters of interest because the measurement approach is inherently unstable and, therefore, the sensors may exhibit significant deviations or drifts away from the true value. Sampling apparatus 10 compensates for naturally-occurring sensor drift and error by self-calibrating the inherently unstable sensors on a frequent, repetitive basis.

The process is controlled by special calibration software in computer 562, which initiates a set of commands that first switch the system into the calibration mode. A calibration file is then generated from a series of pulses of the calibrating reagent (or reagents). The concentration in these pulses is controlled by computer 562 which relays a constant voltage and current spike to the anti-fouling electrodes 59 (at end 58 of probe 54). This results in the electrochemical production of a complex mixture of chemical agents, which alter the characteristics of the sampled water to the extent that a significant signal spike is observed for the downstream sensors in the sampled water.

Although all sensors (i.e., salinity, oxygen, pH, Eh, Chlorophyll fluorescence, temperature, and optical attenuation) show a response, the halogen pulse represents a surrogate calibrant instead of the actual material being measured. Nevertheless, the surrogate calibrant provides a controlled, repeatable pulse of reagent to test the performance characteristics of the entire analytical system. Therefore, response time is tested by measuring the time interval between the pulse initiation and the sensor response for fast responding sensors. This result is used to evaluate the performance of the pump and entire flow path. This is an important consideration for high speed vessels or sensors having delayed response times, since the vessel can be a considerable distance from the actual point of sampling by time the delayed sensor signal is recorded.

Figure 17:
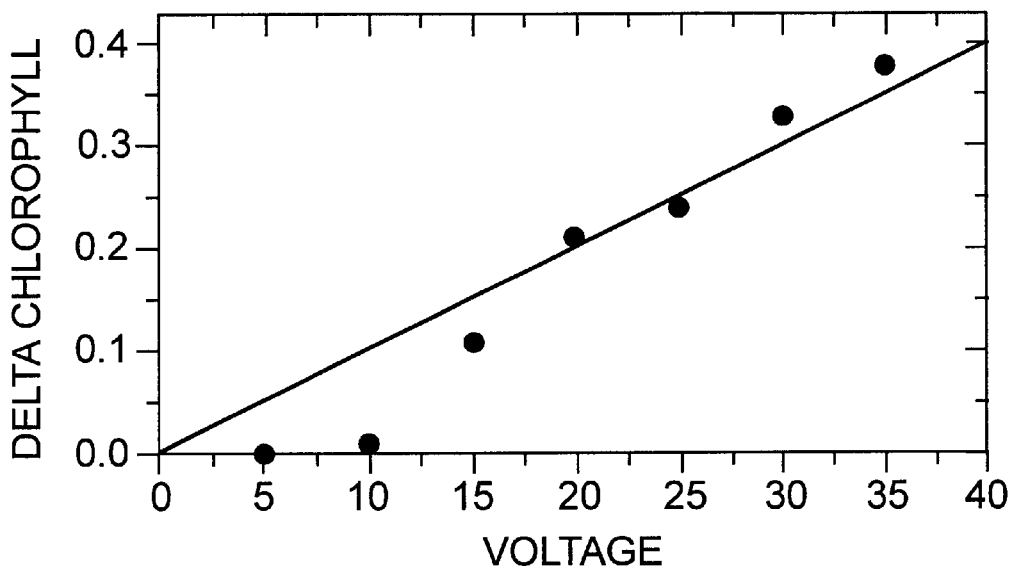
FIG. 17 is a graphical illustration of a first calibration curve utilized by the present invention, showing the linear relationship between voltage and Chlorophyll readings.
Figure 18:
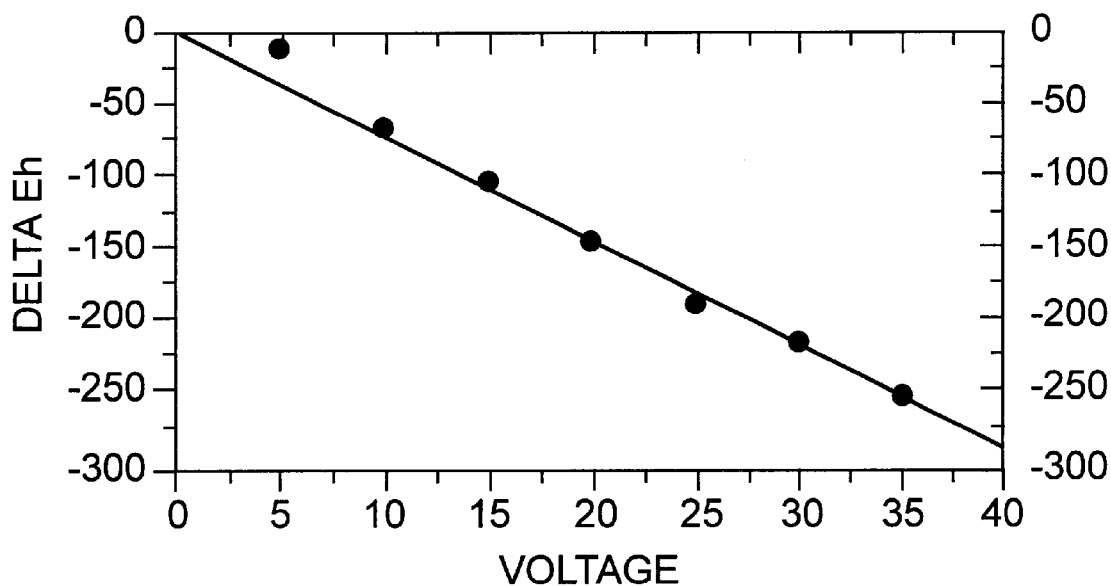
FIG. 18 is a graphical illustration of a second calibration curve utilized by the present invention, showing the linear relationship between voltage and Eh readings.

Sensor calibration is performed by producing a sequential series of increasing concentrations of the electrochemically produced calibrant. This is accomplished through generation of a series of pulses with sequentially increasing voltage as controlled by the computer 562. As shown in FIGS. 17 and 18, which illustrate electrochemically-generated calibration curves for Eh and chlorophyll sensors, there is a linear correlation between the detector response and voltage after a certain threshold voltage is exceeded.

Once generated, the calibration curves are used to evaluate the performance of the sensor and, when possible, update the data calculation file with the slope from the new calibration curve. If this is not possible, the data is tagged as suspect and the sensor is re-calibrated by standard methods. This is either done by personnel at the site of module 10, or in the case of ship 16 without trained personnel, when ship 16 makes a port stop.

In some applications, the calibration is done by injecting precise amounts of calibration reagent into the base of liquid manifold 524. In this mode, a special computer controlled reagent dispenser sub-module is installed. This sub-module contains a stepper motor delivery system and the reagents. Like other sub-modules, the dispenser sub-module can be easily added, removed, or exchanged.

The management and supervisory software for sampling apparatus 10 is a modified version of SCS data collection software developed by the National Oceanic and Atmospheric Administration (NOAA). Once gathered by computer 562 in module 10 using this modified NOAA software, the data preferably is formatted and transmitted in real time via satellite utilizing specially developed and unique telemetry software compatible with INMARSAT C, GOES, ORBCOMM or other satellite communications equipment. This special telemetry manages the compression and formatting of outgoing binary messages and decodes and implements any incoming management data. In some fixed applications, telephone land line, VHF radio, or cellular phone data links are also possible.

The management and supervisory software and the telemetry software have been developed or tailored specifically for sampling apparatus 10. The software is organized into several different sections and then different sub-sections.

One set of software gathers data from INMARSAT standard C or other satellite transmission systems. It then decodes the received compressed signals, quality controls the information and distributes the data to remote databases, such as governmental and private agencies interested in the data collected.

A second software set resides upon the vessel within the computer 562 and is organized into several components. First, there is a data acquisition and real time display package. This software component polls the sensors at a frequency determined elsewhere and accumulates acquired data to temporary storage prior to telemetry and local display. The local display part of this component permits networked computers on vessel 16 to graph and display, either in real time or from historical databases, time series plots of measured variables in a very flexible manner. Second, there is a data acquisition/system management program. This component receives instructions via satellite regarding system management and control. Functions controlled include, putting computer system in and out of standby condition, starting system pump, initiating adaptive operations based upon values of measured variables initiating and controlling calibration and anti-fouling cycles. Third, there is a data telemetry and management message reception software component. This component manages the compression and formatting of outgoing binary messages and decodes and implements the incoming management data.

Software also permits two-way communication with sampling apparatus 10 so that the Module can be given instructions, new testing protocols, etc. This two-way communication feature is very different to anything to be found upon existing water monitoring devices such as on current drifters, buoys and research ships that offer only one-way communications and therefore cannot be directed controlled, adjusted or calibrated remotely.

Finally, the overall data system includes a set of decision trees that allow the system to respond to events or spikes reflected in the data being collected and transmitted. More routine data systems involve the storage of data and the reporting of events to nodes. In the data system, however, if a toxic algal bloom or a plume event is detected the data system will initialize a response by contacting appropriate users or sites while at the same time contacting sampling apparatus 10 producing the data requesting it to re-run samples or retest an area. Similarly, when detected wind speeds exceed a certain level the system is programmed to sample and transmit all weather data every hour rather than every three hours which is the normal interval for weather forecast modeling.

Figure 19:
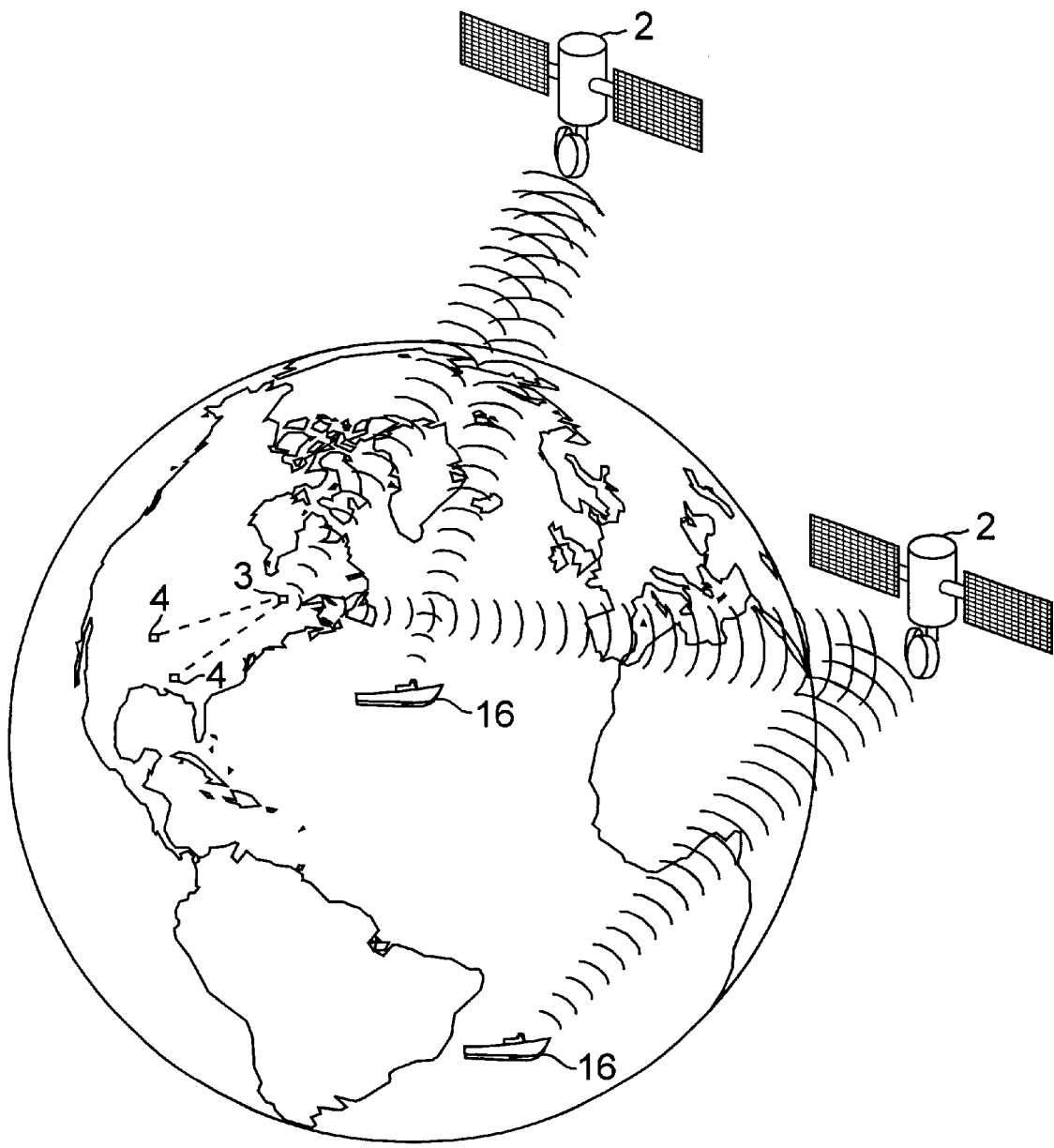
FIG. 19 is a schematic illustration of a global water monitoring system according to the present invention.

FIG. 19 illustrates an overall system of the present invention, including vessels 16, which take data at various locations around the world. For example, sampling apparatus 10 may be employed on a variety of ocean and lake going vessels including research ships, cruise ships, naval ships, trawlers, fishing boats, and tankers. It may also be deployed on buoys, piers and other platforms. Each of sampling apparatus 10 (e.g., on vessels 16) may transmit their data via satellites 2 to a central computer 3. That data may then be accessed by parties 4 interested in analyzing that data. In addition, central computer 3 may send signals to any individual sampling apparatus 10 to take particular measurements when vessel 16 enters a particular global region.

The primary purpose of the above uses will be to generate significant new data on the oceans conditions to be used for improved weather forecasting, enhanced climatic change monitoring, education (GLOBE program) and improved fisheries management. The data will also be used to ground truth data from ocean sensors on orbiting satellites, and to assist in the calibration of such sensors.

Finally, it is contemplated that sampling apparatus 10 may be used on oil drilling platforms, in aquaculture facilities (to detect changes in salinity levels, the presence of preconditions to toxic algal blooms, and other conditions hazardous to sea life), to monitor fresh water lakes, rivers, streams, and reservoirs (for algae and bacterial growth), to monitor sewer out falls, storm drains, and other ocean discharge sources for heavy metal contamination, to monitor pollution in harbors, to monitor sanitary conditions in public swimming pools, and to monitor waste water treatment facilities and holding tanks.

While specific embodiments of the present invention have been disclosed, those skilled in the art will readily recognize that many of the components described and illustrated may be substituted with similar components without deviating from the scope and spirit of the present invention. Accordingly, it is intended that the claims appended hereto encompass all equivalents thereto and are not limited by the embodiments disclosed herein.

What is claimed is:

1. A water sampling apparatus, comprising:

a water inlet;

a pump, in fluid communication with the water inlet, for drawing a water sample from a body of water through the water inlet;

a plurality of plug-in testing units, in fluid communication with the pump and the water inlet, for determining characteristics of a the water sample, the plurality of plug-in testing units being contained within a dry instrument module;

a plurality of electrical components, in communication at least with some of the plurality of plug-in testing units, for generating data signals concerning the characteristics of the water sample, the plurality of electrical components being contained within a computer module;

a computer, in communication at least with some of the plurality of electrical components, for collecting the data signals generated by the plurality of electrical components and for providing the data signals to a database; and a water outlet, in fluid communication with the plurality of plug-in testing units, for returning the water sample to the body of water.

2. The sampling apparatus of claim 1, wherein the computer is located within the computer module.

3. The sampling apparatus of claim 1, wherein the database is located in at least one of a memory in the computer or a memory in a computer located remotely from the sampling apparatus.

4. The sampling apparatus of claim 1, wherein the plurality of plug-in testing units determine characteristics for at least one of salinity, water temperature, dissolved oxygen content, pH, Eh, Chlorophyll content, CDOM, turbidity, meteorological conditions, global position, bioluminescence, toxic metal content, phosphate content, silicate, $pCO_2$, biochemical content, ozone content, and solar radiation.

5. The sampling apparatus of claim 4, wherein the plurality of plug-in testing units operate autonomously according to a predetermined program within the computer.

6. The sampling apparatus of claim 1, wherein the computer automatically periodically calibrates the plurality of plug-in testing units to compensate for measurement error.

7. The sampling apparatus of claim 1, wherein the computer automatically and periodically performs a n anti-fouling operation to minimize accumulation of biofouling agents.

8. The sampling apparatus of claim 1, wherein the apparatus is positioned in or near the body of water and is on at least one of a sea-going vessel, a buoy, a drifter, a trawler, a research vessel, a private yacht, a commercial boat, a tanker, a fishing boat, a pier, a floating platform, a naval vessel, or an oil-drilling platform.

9. The sampling apparatus of claim 1, wherein the body of water includes at least one of a lake, a sea, an ocean, a stream, a river, or a reservoir.

10. A vessel, comprising:
   a hull for supporting the vessel in a body of water;
   a water inlet disposed through the hull;
   a pump, in fluid communication with the water inlet, for drawing a water sample from the body of water through the water inlet;
   a plurality of plug-in testing units, in fluid communication with the pump and the water inlet, for determining characteristics of a the water sample, the plurality of plug-in testing units being contained within a dry instrument module within the hull;
   a plurality of electrical components, in communication at least with some of the plurality of plug-in testing units, for generating data signals concerning the characteristics of the water sample, the plurality of electrical components being contained within a computer module within the hull;
   a computer, in communication at least with some of the plurality of electrical components, for collecting the data signals generated by the plurality of electrical components and for providing the data signals to a database; and
   a water outlet, in fluid communication with the plurality of plug-in testing units, for returning the water sample to the body of water.

11. The vessel of claim 10, wherein the computer is located within the computer module.

12. The vessel of claim 10, wherein the database is located in at least one of a memory in the computer or a memory in a computer located remotely from the sampling apparatus.

13. The vessel of claim 10, wherein the plurality of plug-in testing units determine characteristics for at least one of salinity, water temperature, dissolved oxygen content, pH, Eh, Chlorophyll content, CDOM, turbidity, meteorological conditions, global position, bioluminescence, toxic metal content, phosphate content, silicate, $pCO_2$, biochemical content, ozone content, and solar radiation.

14. The vessel of claim 10, wherein the plurality of plug-in testing units operate autonomously according to a predetermined program within the computer.

15. The vessel of claim 10, wherein the computer automatically and periodically calibrates the plurality of plug-in testing units to compensate for measurement error.

16. The vessel of claim 10, wherein the computer automatically and periodically performs an anti-fouling operation to minimize accumulation of biofouling agents.

17. The vessel of claim 10, wherein the body of water includes at least one of a lake, a sea, an ocean, a stream, a river, or a reservoir.

18. The vessel of claim 10, further comprising:
   a scoop, disposed exterior to the hull, with an opening therethrough defining the water inlet; and
   at least one break away bolt connecting the scoop to the hull, the at least one break away bolt shearing upon application of more than a predetermined force on the scoop;
   wherein the opening is displaced a predetermined distance from the hull to minimize at least one of ingestion of debris, ingestion of bubbles, or cavitation,
   wherein the scoop has a curved surface to minimize drag in the body of water, and
   wherein the scoop has venting holes to eliminate excess water from the system and reduce bubbles in the water stream.

19. The vessel of claim 18, further comprising:
   a sieve, positioned over the opening and at a predetermined angle, for minimizing at least one of ingestion of debris, ingestion of bubbles, or cavitation.

20. The vessel of claim 19, wherein the predetermined angle is 45 degrees.

21. The vessel of claim 10, further comprising:
   a sensor, disposed within the instrument module, for generating a warning signal if water is present in the instrument module;
   a solenoid valve, disposed downstream of the water inlet, for closing the water inlet upon receipt of the warning signal; and
   a containment vessel, disposed just inside of the hull and surrounding the solenoid valve, for preventing water from entering the hull if a leak develops between the hull and the solenoid valve.

22. A system for sampling water at locations around the world, comprising:
   a plurality of vessels, each having
      a hull for supporting the vessel in a body of water,
      a water inlet disposed through the hull,
      a pump, in fluid communication with the water inlet, for drawing a water sample from the body of water through the water inlet,
      a plurality of plug-in testing units, in fluid communication with the pump and the water inlet, for determining characteristics of a the water sample, the plurality of plug-in testing units being contained within a dry instrument module within the hull,
      a plurality of electrical components, in communication at least with some of the plurality of plug-in testing units, for generating data signals concerning the characteristics of the water sample, the plurality of electrical components being contained within a computer module within the hull,
      a computer, in communication at least with some of the plurality of electrical components, for collecting the data signals generated by the plurality of electrical components and for providing the data signals to a database, and
      a water outlet, in fluid communication with the plurality of plug-in testing units, for returning the water sample to the body of water;
   a plurality of transmitters aboard the plurality of vessels for transmitting the data signals;
   at least one orbital satellite for collecting data signals from the plurality of transmitters and for re-transmitting the data signals; and
   a remote computer for receiving the data signals from the at least one satellite and for compiling the data signals into the database.

* * * * *